(12) United States Patent
    Jobert

(10) Patent No.: US 12,152,235 B2
(45) Date of Patent: Nov. 26, 2024

(54) METHODS AND COMPOSITIONS FOR COUPLING NUCLEIC ACID TO A FUNCTIONALIZED SUPPORT

(71) Applicant: LIFE TECHNOLOGIES AS, Oslo (NO)

(72) Inventor: Laure Jobert, Hosle (NO)

(73) Assignee: Life Technologies AS, Oslo (NO)

( * ) Notice: Subject to any disclaimer, the term of this patent is extended or adjusted under 35 U.S.C. 154(b) by 0 days.

(21) Appl. No.: 18/069,171

(22) Filed: Dec. 20, 2022

(65) Prior Publication Data

US 2023/0295605 A1   Sep. 21, 2023

Related U.S. Application Data

(62) Division of application No. 16/645,896, filed as application No. PCT/EP2018/073353 on Aug. 30, 2018, now Pat. No. 11,555,183.

(30) Foreign Application Priority Data

Sep. 11, 2017 (GB) ...................................... 1714563

(51) Int. Cl.
    *C12N 15/10* (2006.01)
(52) U.S. Cl.
    CPC ................ *C12N 15/1013* (2013.01)
(58) Field of Classification Search
    CPC .................................................. C12N 15/1013
    See application file for complete search history.

(56) References Cited

U.S. PATENT DOCUMENTS

2013/0344567 A1   12/2013  Boschetti et al.

FOREIGN PATENT DOCUMENTS

| EP | 1256626 A1 | 11/2002 |
|----|------------|---------|
| JP | 2008134259 A | 6/2008 |
| WO | WO-2006138560 A2 | 12/2006 |
| WO | WO-2009020609 A2 | 2/2009 |

OTHER PUBLICATIONS

Franzini et al. Bioconjugate Chemistry, 2014, 25, 1453-1461. (Year: 2014).*
Chu et al., "Detection of specific DNA sequences with short biotin-labeled probes", DNA, vol. 4, No. 4, Aug. 1985, pp. 327-331.
Devor et al., "Strategies for Attaching Oligonucleotides to Solid Supports", Integrated DNA Technologies, Jan. 2005 (Jan. 1, 2005), XP055294450, Retrieved from the Internet: URL:https://www.idtdna.com/pages/docs/default-source/technical-reports/strategies-for-attaching-oligonucleotides-to-v6-03-14-14.pdf?sfvrsn=2 [retrieved on Aug. 9, 2016].
Dynabeads® M-270 Carboxylic Acid Catalog Nos. 14305D, 14306D manual, Jun. 2012.
Dynabeads® MyOne™ Carboxylic Acid Catalog Nos. 65011, 65012, manual, Jun. 2013.
Ghosh SS et al., "Covalent attachment of oligonucleotides to solid supports.", Nucleic Acids Research, vol. 15, No. 13, Jul. 1987, pp. 5353-5372.
Li Y et al., "Optimized Reaction Conditions for Amide Bond Formation in DNA-Encoded Combinatorial Libraries", ACS Combinatorial Science, vol. 18, No. 8, Jun. 23, 2016, pp. 438-443.
Li et al., "Optimized Reaction Conditions for Amide Bond Formation in DNA-Encoded Combinatorial Libraries", ACS Combinatorial Science, vol. 18, No. 8, Jun. 23, 2016, pp. 438-443, Supplement Material.
Nakajima N., et al., "Mechanism of Amide Formation by Carbodiimide for Bioconjugation in Aqueous Media," Bioconjugate Chemistry, 1995, vol. 6, pp. 123-130.
PCT/EP2018/073353, Search Report and Written Opinion, Jan. 28, 2019, 20 pages.

* cited by examiner

*Primary Examiner* — Jezia Riley
(74) *Attorney, Agent, or Firm* — Vijay Gore

(57) ABSTRACT

This invention relates to methods and compositions for coupling nucleic acid to a functionalized surface or support. In particular, the present invention provides an improved process for coupling aminated nucleic acid to a support functionalized with carboxylic acid groups, wherein the coupling reaction is conducted in the presence of an organic solvent. The invention further relates to compositions and kits for performing the coupling reaction and uses of nucleic acid-loaded supports for various applications.

17 Claims, 6 Drawing Sheets

Specification includes a Sequence Listing.

METHODS AND COMPOSITIONS FOR COUPLING NUCLEIC ACID TO A FUNCTIONALIZED SUPPORT

CROSS-REFERENCE

This application is a divisional of U.S. application Ser. No. 16/645,896 filed on Mar. 10, 2020 which is a 371 US National Phase Entry Application of International Application No. PCT/EP2018/073353 filed Aug. 30, 2018, which claims the benefit GB Application No. 1714563.2 filed Sep. 11, 2017. The entire contents of the aforementioned applications are incorporated by reference herein.

SEQUENCE LISTING

The instant application contains a Sequence Listing which has been submitted electronically in ASCII format and is hereby incorporated by reference in its entirety. Said ASCII copy, created on Dec. 16, 2022 is named TP103468USDIV1_SL.ST.26 XML and is 5,550 bytes in size.

The present invention relates to methods and compositions for coupling nucleic acid to a functionalized surface or solid support. In particular, the present invention relates to methods and compositions for coupling aminated nucleic acid to a support that is functionalized with carboxylic acid groups, and uses of such modified supports for various applications.

BACKGROUND

Nucleic acid(s) may be immobilized on solid supports for various applications including on-support chemical or enzymatic nucleic acid synthesis, sequencing reactions, affinity chromatography for purifying substances, or hybridization assays used in in vitro diagnostics to identify and quantify very small amounts of targets. Immobilized nucleic acids are frequently used to specifically isolate target ligands from complex mixtures or biological samples where the nucleic acids are designed to selectively hybridize to the desired target molecule.

Various types of materials suitable for immobilizing nucleic acid are known in the art including nylon, nitrocellulose, activated agarose, diazotized cellulose, latex particles, plastic, polystyrene, glass and polymer coated surfaces. These materials are used in many formats such as membranes, plates, slides, chip, resin, beads, probes, microtiter plates, dipsticks etc. A wide variety of chemical modifications are available for covalent coupling of nucleic acids (either directly or through a linker) to these carriers which are often referred to as (solid) support. To allow binding of the nucleic acid molecule, the support is typically functionalized to expose nucleophilic groups that react with a reactive group on the nucleic acid. Alternatively, a reactive group is introduced into the support to react with a nucleophile present in the nucleic acid. Suitable groups or moieties include hydroxyl, sulfhydryl, amino and activated carboxylic acid groups, while the groups capable of reacting with these include dichlorotriazinyl, alkylepoxy, maleimido, bromoacetyl groups and others. Strategies for coupling nucleic acids to different types of functionalized solid supports are described e.g. in Gosh and Musso (Nuc. Acid Res., 15(13), 5353-5372, 1987) or Devor et al. (*"Strategies for Attaching Oligonucleotides to Solid Supports"*, Integrated DNA Technologies, 2005). Dependent on the presence of either a reactive or nucleophilic group on the solid support and the nucleic acid molecule, coupling can either be performed directly or with bifunctional reagents or cross-linkers. Bifunctional and coupling reagents are well known in the art and are available from commercial sources such as Thermo Fisher Scientific, Sigma-Aldrich, ProteoChem etc.

One widely used type of surface chemistry for attachment of nucleic acid to a solid support is carboxylic acid functional groups. Surfaces with carboxylic acid functional groups may in general be provided by treating the uncoated surface (e.g. uncoated polymer particles) with a polymer or copolymer of acrylic acid or methacrylic acid carrying such carboxylic acid groups. For example, solution copolymerisation with methacrylic acid yields a polymeric coating carrying terminal carboxyl groups. To allow covalent coupling to a carboxylic acid coated surface, the nucleic acid is typically modified with a functional reactive group. For example, the nucleic acid may be provided with a primary amino group at its 5' or 3' end to allow coupling of the aminated molecule with an activated carboxylate surface (e.g. using carbodiimide chemistry), which results in a covalent carbonyl amide linkage. Alternatively, the nucleic acid may be provided in thiol-modified form and may be covalently linked to a maleimide-modified surface via an alkylating agent.

Many applications strive for a highly efficient coupling process to allow for quantitative loading of nucleic acids onto a given support, which facilitates the predictability of coupling yields and thus, the reliability of coupling reactions. However, the coupling efficiency achieved by methods known in the art is limited when standard procedures are used to couple aminated nucleic acids to carboxylic acid functionalized support in aqueous buffer (for example by using carbodiimide chemistry to activate the carboxylic acid groups). The low coupling efficiency is often compensated for by providing increased amounts of nucleic acid to obtain adequate yields of immobilized nucleic acid. Another frequently observed disadvantage of standard coupling procedures is the high rate of non-specific coupling events via internal secondary amine groups of the nucleic acids or unfavorable hybridization kinetics of the immobilized oligonucleotide, both of which may lead to a high background in various assays.

Thus, there is a general desire to develop methods with improved coupling efficiency that result in high and predictable yields of surface-bound nucleic acid without the need to increase the amount of nucleic acid molecules added to the coupling reaction.

One object of the current invention is therefore to provide compositions and methods that allow for coupling of nucleic acid to a solid support at higher efficiency. A further object of the invention is to provide compositions and methods that reduce the amount of nucleic acid required to achieve a desired coupling yield. Another object of the invention is to provide compositions and methods that reduce the non-specific coupling of nucleic acid molecules to a solid support.

SUMMARY OF THE INVENTION

State of the art procedures for coupling nucleic acid on carboxylate functionalized supports suffer from low coupling efficiencies and impractical amounts of nucleic acid required to reach adequate levels of coupling yields. The inventors have surprisingly found that the coupling efficiency can be significantly improved when the activation and coupling reaction is conducted in organic phase (i.e. in the presence of an organic solvent), thereby at the same time reducing non-specific coupling.

The invention therefore relates, in part, to methods and compositions for coupling of nucleic acid to a solid support. In particular the invention seeks to improve the coupling efficiency of aminated nucleic acid molecules to solid surfaces functionalized with carboxylic acid groups. It has been recognized that these objects can be met by conducting both, the activation and the coupling reaction in the presence of an organic solvent. It has further been recognized that unspecific coupling can be further reduced by adding salt to the coupling reaction.

A first aspect of the present invention therefore provides a method for coupling a nucleic acid molecule to a support comprising (a) providing a support comprising thereon carboxylic acid groups, (b) providing a nucleic acid, wherein the nucleic acid comprises at least one primary amine function, (c) activating the support by contacting the carboxylic acid groups thereon with a carbodiimide or a derivative thereof, to form a reactive anhydride, (d) reacting the reactive anhydride with the at least one primary amine function of the nucleic acid to form a covalent amide bond, thereby coupling said nucleic acid to the support, wherein steps (c) and (d) are conducted in the presence of an organic solvent. In some embodiments, steps (c) and (d) are conducted in the presence of a salt. A method according to the first aspect may further comprise (e) separating the coupling solution of step (d) and the support and washing the support.

A second aspect of the present invention provides a composition for coupling nucleic acid to a functionalized support. In a first embodiment, the composition comprises a support comprising thereon carboxylic acid groups, a nucleic acid comprising at least one primary amine function, a carbodiimide or derivative thereof, and an organic solvent. In a second embodiment, the composition comprises a support comprising thereon carboxylic acid groups, wherein at least a first portion of the carboxylic acid groups is modified with a reactive anhydride and at least a second portion of the carboxylic acid groups is bonded to a nucleic acid via a carbonyl-amide bond, an organic solvent, and optionally an isourea by-product. In a third embodiment the composition comprises a support comprising thereon carboxylic acid groups bonded to a nucleic acid via a carbonyl-amide bond, and an organic solvent, wherein the support is beads having a nucleic acid coupling density of between about 10 and about 10,000 pmol/mg support or between about 50 and about 5,000 pmol/mg support.

A third aspect of the present invention provides a kit for coupling nucleic acid to a solid support comprising a support comprising thereon carboxylic acid groups, an organic solvent, a carbodiimide or derivative thereof, and optionally, a nucleic acid.

The methods, compositions and kits of the invention are not limited to the subject matter just mentioned but are, without limitation, described more fully in the following description and claims.

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying Figures.

DETAILED DESCRIPTION

Figure 1:
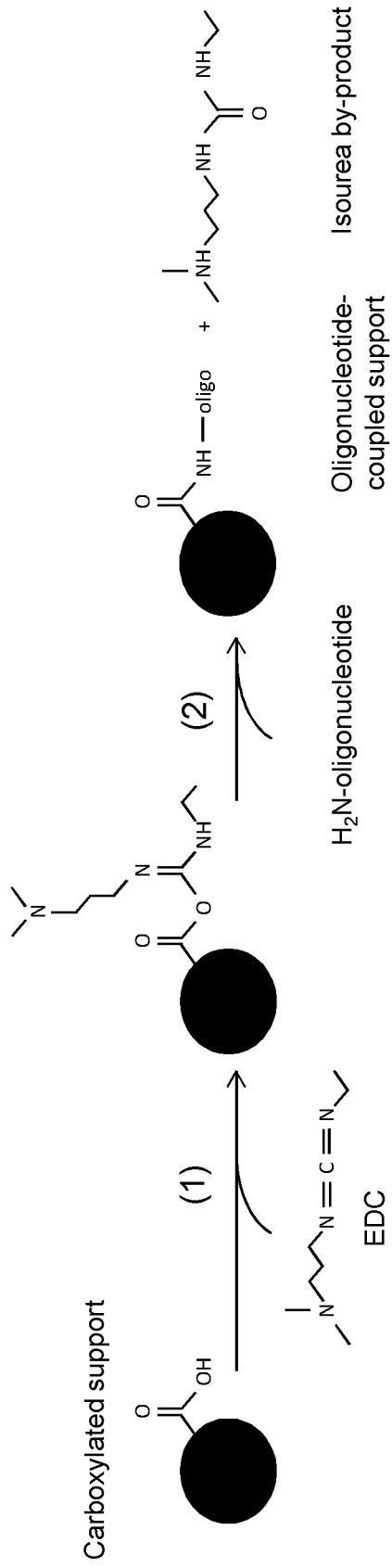
FIG. 1 is a schematic of an exemplary coupling procedure comprising coupling of an aminated oligonucleotide to a solid support functionalized with carboxylic acid groups.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

It will be appreciated that where an "about" is used prior to the temperatures, concentrations, amounts, times, numbers, ranges, coverage, etc. discussed in the present teachings, slight and insubstantial deviations are within the scope of the present teachings.

Concentrations given as percentage values are understood to indicate volume percent, unless explicitly stated otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any embodiments disclosed herein. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

All publications, patent applications, patents, and other references mentioned herein are incorporated by reference in their entirety. In case of conflict, the present specification, including definitions, will control.

Aspects of the invention including exemplary methods, compositions and uses as well as preferred embodiments are hereinafter described in more detail.

In a first aspect, the disclosed methods and compositions provide a support for coupling nucleic acids thereon.

The term "nucleic acid" or "nucleic acids" or "nucleic acid molecule(s)" as used herein refers to one or more covalently linked sequence of nucleotides or bases (e.g., ribonucleotides for RNA and deoxyribonucleotides for DNA but also include DNA/RNA hybrids where the DNA is in separate strands or in the same strand) in which the 3' position of the pentose of one nucleotide is joined by a phosphodiester linkage to the 5' position of the pentose of the next nucleotide. Nucleic acid may be single- or double-stranded or partially double-stranded, may be linear or circularized. Nucleic acid may be composed of completely complementary single strands or of partially complementary single strands.

A nucleic acid has a "5'-terminus" and a "3'-terminus" because nucleic acid phosphodiester linkages occur between the 5' carbon and 3' carbon of the pentose ring of the substituent mononucleotides. The end of a nucleic acid at which a new linkage would be to a 5' carbon is its 5' terminal nucleotide. The end of a nucleic acid molecule at which a new linkage would be to a 3' carbon is its 3' terminal nucleotide. A terminal nucleotide or base, as used herein, is the nucleotide at the end position of the 3' or 5' terminus. Nucleic acids also refer to shorter nucleic acid molecules, often referred to as, for example, primers or probes as discussed below. Also, the terms "5'" and "3'" refer to strands of nucleic acids. Thus, a linear, single stranded nucleic acid will have a 5' terminus and a 3' terminus. However, a linear, double stranded nucleic acid will have a 5' terminus and a 3' terminus for each strand.

Nucleic acids used in various embodiments may comprise chemically, enzymatically, or metabolically modified forms of nucleotides or combinations thereof. Chemically synthesized nucleic acid molecules may refer to nucleic acids typically less than or equal to 200 nucleotides long (e.g., between 5 and 200, between 10 and 150, between 15 and 100, or between 20 and 50 nucleotides in length), whereas enzymatically synthesized nucleic acid molecules may encompass smaller as well as larger nucleic acid molecules. Enzymatic synthesis of nucleic acid molecules may include stepwise processes using enzymes such as polymerases, ligases, exonucleases, endonucleases, recombinases or the like or a combination thereof.

Nucleic acids according to various embodiments may comprise conformationally restricted or nucleobase analogue-bearing oligomers such as "locked-nucleic acids" (LNA) or "peptide nucleic acids" (PNA). LNA comprise a conformationally restricted nucleotide analogue with an extra 2'-O, 4'-C-methylene bridge added to the ribose ring that "locks" the ribose in the 3'-endo conformation. The synthesis and incorporation of LNA bases can be achieved by using standard DNA synthesis chemistry. Synthetic procedures for locked nucleic acids are described e.g. in Singh et al. (Chem. Comm. 455-456, 1998) and Wengel J. (Ace. Chem. Res., 32, 301-310, 1998). Specific types of LNA phosphoramidites have been reported e.g. in U.S. Pat. No. 6,268,490. LNA are resistant to exo- and endonucleases resulting in high stability in in vivo and in vitro applications. LNA-containing oligonucleotides have been shown to bind double-stranded plasmid DNA in a sequence-specific manner. The high binding affinity of LNA oligonucleotides allows for the use of LNA in probes for binding or hybridization based assays and in particular as short probes in antisense protocols. In particular LNA may be useful in any hybridization assay that requires high specificity and/or reproducibility, e.g., dual labeled probes, in situ hybridization probes, molecular beacons and PCR primers. Furthermore, LNA offers the possibility to adjust melting temperature (Tm) values of primers and probes in multiplex assays. Each LNA base addition in an oligonucleotide increases the Tm by up to 80° C. As a result of these significant characteristics, LNA-modified nucleic acids (e.g. oligonucleotides) are increasingly used in antisense drug development.

The term "PNA" as used herein, relates to a peptide nucleic acid, i.e. an artificially synthesized polymer similar to DNA or RNA which is used in biological research and medical treatments, but which is not known to occur naturally. In PNA compounds the sugar-backbone of an oligonucleotide is replaced with an amide containing backbone and is typically composed of repeating N-(2-aminoethyl)-glycine units linked by peptide bonds. The various purine and pyrimidine bases are linked to the backbone by methylene carbonyl bonds. The nucleobases are retained and are bound directly or indirectly to aza nitrogen atoms of the amide portion of the backbone. PNAs are generally depicted like peptides, with the N-terminus at the first position and the C-terminus at the last position (from left to right). Representative patents that teach the preparation of PNA compounds comprise, but are not limited to, U.S. Pat. Nos. 5,539,082; 5,714,331; and 5,719,262. Further teaching of PNA compounds can be found in Nielsen et al. (Science, 254, page 1497, 1991). PNA has been shown to retain hybridization properties. Furthermore, it has been shown that PNA duplexes show unaffected stability in solvent comprising high amounts of DMSO (Sen A. and Nielsen P E, Nucleic Acids Res., 35, 3367-3374, 2007), which makes PNA a particularly suitable candidate for coupling to solid support in organic solvent according to various embodiments.

The term nucleic acid as used herein comprises oligonucleotides, primers, probes, and aptamers as further defined below.

The term "oligonucleotide" or "oligo", as used herein, refers to DNA, RNA and nucleobase analogue containing oligomers (including LNA or PNA as described above), and to any other type of nucleic acid that is an N-glycoside of a purine or pyrimidine base but will typically be DNA. Oligonucleotides are thus a subset of nucleic acids and may be single stranded or double stranded. Oligonucleotides may have a length ranging from at least 2, or generally about 5 to about 200, or more commonly from about 20 to about 100 nucleotides. Oligonucleotides are often less than 200 nucleotides, more typically less than 100 nucleotides in length. Thus, "primers" will generally fall into the category of oligonucleotide. In addition, oligonucleotides may be nuclease resistant and include but are not limited to 2'-0-methyl ribonucleotides, phosphorothioate nucleotides, phosphorodithioate nucleotides, phosphoramidate nucleotides, and methylphosphonate nucleotides.

Oligonucleotides may be synthetic and may be modified at one or both or their 5' or 3' terminal ends. Oligonucleotides may comprise additional functional groups or molecules (or atoms) that have been joined, either covalently or non-covalently. These additional groups or molecules (or atoms) may be attached to virtually any site on the oligonucleotide depending on downstream application and may be used for attaching ligands to oligonucleotides and/or for coupling oligonucleotides to a solid surface. For example, an oligonucleotide may be modified by attaching one or more terminal reactive amine functions as discussed below, resulting in an amine-modified or amino-modified or aminated oligonucleotide, and these terms may be used interchangeably herein.

Oligonucleotides can be prepared by any suitable method, including direct chemical synthesis by a method such as the phosphotriester method of Narang et al. (Meth. Enzymol. 68, 90-99, 1979); the phosphodiester method of Brown et al. (Meth. Enzymol. 68, 109-151, 1979); the diethylphosphoramidite method of Beaucage et al. (Tetrahedron Letters 22, 1859-1862, 1981); and the solid support method of U.S. Pat. No. 4,458,066. A review of synthesis methods of conjugates of oligonucleotides and modified nucleotides is provided in Goodchild (Bioconjugate Chemistry 1, 165-187, 1990). Where appropriate, the term oligonucleotide may refer to a primer or probe or ligand and these terms may be used interchangeably herein.

The term "primer" or "probe", as used herein, refers to a short nucleic acid capable of at least partially hybridizing with a target nucleic acid under suitable conditions. The term "hybridization", as used herein, refers to any process by which a strand of nucleic acid binds with a complementary strand through base pairing. Hybridization and the strength of hybridization (for example, the strength of the association between the nucleic acids) is impacted by such factors as the degree of complementarity between the nucleic acids, stringency of the conditions involved, the Tm of the formed hybrid, and the G:C ratio within the nucleic acids.

Whereas a probe is typically designed to hybridize with a sequence in a target molecule and detectably labeled, a primer is often referred to as starter nucleic acid molecules for enzymatic assembly reactions.

For primers, such conditions include those in which synthesis of a primer extension product complementary to a nucleic acid strand is induced in the presence of different nucleoside triphosphates (e.g., A, C, G, T and/or U) and an agent for extension (for example, a DNA polymerase or reverse transcriptase) in an appropriate buffer and at a suitable temperature. A primer or probe is generally composed of single-stranded DNA but can be provided as a double-stranded molecule for specific applications. Optionally, a primer or probe can be naturally occurring or synthesized using chemical synthesis of recombinant procedures.

The appropriate length of a primer or probe depends on its intended use but typically ranges from about 5 to about 200 nucleotides, including intermediate ranges, such as from about 10 to about 50 nucleotides, from about 15 to about 35 nucleotides, from about 18 to about 75 nucleotides, from about 20 to about 120, and from about 25 to about 150 nucleotides. The design of suitable primers or probes for selected applications is well known in the art and described in the literature (see for example OligoPerfect™ Designer, Thermo Fisher Scientific). Primers or probes can incorporate additional features which allow for the detection or immobilization of the primer or probe but do not alter the basic property or functionality. For example, a probe can have modifications, such as a 3' terminus modification that makes the probe non-extendable by nucleic acid polymerases, and one or more chromophores. An oligonucleotide with the same sequence may serve as a primer in one assay and a probe in a different assay. An oligonucleotide having specific binding properties with respect to a target molecule may also be referred to as a "ligand".

In some embodiments, a nucleic acid may be an aptamer. The term "aptamer" as used herein is a single-stranded nucleic acid (DNA or RNA) which binds specifically to one or more target molecules (e.g. a protein or peptide). The aptamers encompass those for which it is possible to detect complexes with a single given target molecule or with a variety of given target molecules, after a prior step of bringing the respective nucleic acid and target molecule partners into contact. Aptamers bind to their target molecules via mechanisms which are essentially distinct from hybridization. Aptamers are generally characterized by a secondary structure comprising loops and stems. In other words, the active conformation of aptamers (i.e. the conformation in which aptamers are capable of binding to their target protein) is nonlinear.

Aptamers generally comprise between 5 and 120 nucleotides and can be selected in vitro according to a process known as SELEX (Systematic Evolution of Ligands by Exponential Enrichment). Aptamers have many advantages. By virtue of their oligonucleotide nature, aptamers have a low immunogenicity and high resistance to stringent physicochemical conditions (presence of urea, of DMSO, of a very acid or of a very basic pH, use of organic solvents or of a high temperature) enabling varied sanitization strategies in the context of use as an affinity ligand. Furthermore, they have high selectivity. Finally, the production of aptamers involves relatively limited costs. In some embodiments, an aptamer can comprise a non-nucleotide or nucleotide part, for example a non-nucleotide spacer chain as discussed below, which links one of the 5' or 3' termini of the nucleic part of said aptamer and a reactive amine function used for the coupling to a pre-activated support.

The nucleic acid according to various embodiments can have any structure or chemistry as described above and may comprise primers, probes or aptamers which are collectively hereinafter referred to as oligonucleotides. Oligonucleotides coupled to a solid support according to various embodiments may be obtained by various means, including e.g. conventional methods of oligonucleotide synthesis.

Conventional oligonucleotide synthesis methods follow a series of basic steps together often referred to as "synthesis cycle" which may include at least the following exemplary steps b) to f), with appropriate washing steps using one or more solvents such as acetonitrile, ethyl acetate or other washing reagents suitable for practicing solid phase synthesis:

In exemplary step a) a first phosphoramidite, which has been protected at the 5' position (or, in certain embodiments wherein synthesis proceeds in the 5' to 3' direction, the first phosphoramidite may be protected at the 3' position), is derivatized to a solid support such as a polymer particle according to the invention (e.g. by coupling to a universal linker), or is obtained prederivatized as described elsewhere herein;

In exemplary step b), the 5' dimethoxytrityl (DMT) protecting group of the first phosphoramidite (which may be modified or unmodified) is removed, e.g. via detritylation. This process which is often referred to as "deblocking" typically uses an acid such as for example trichloroacetic acid (TCA) or dichloroacetic acid (DCA) in dichloromethane (DCM) or DCA in toluene. Alternatively, electrochemically generated acid ("EGA") or photogenerated acid (PGA) may be used for deprotection. Exemplary EGA or PGA compositions are described e.g. in WO 2013/049227, application No. PCT/US2015/064700 or in Maurer et al., "*Electrochemically Generated Acid and Its Containment to 100*

*Micron Reaction Areas for the Production of DNA Microarrays*", PLoS, 2006, Issue 1, e34.

In exemplary step c) a second phosphoramidite which has the phosphorus, sugar and base groups protected, is added to the deblocked 5'-OH group of the first phosphoramidite. Before the second phosphoramidite is coupled it is typically activated which can be achieved using either an imidazole-type or tetrazole-type catalyst (such as e.g. tetrazole or 4,5-dicyanoimidazole). The activated second phosphoramidite is then reacted with the 5'-OH group of the first phosphoramidite to obtain a trivalent phosphite triester. This process is often referred to as "coupling" and has a general efficiency of above 99% (typically about 99.8%), leaving a very small number of 5'-OH groups unreacted.

In exemplary step d) the unreacted 5'-OH groups of the first phosphoramidites are capped and thereby excluded from subsequent coupling reactions to avoid accumulation of deletions. This process often referred to as "capping" is typically performed by acetylation using, for example, acetic anhydride and N-methylimidazole, preferably in the presence of a base (such as lutidine or pyridine);

In exemplary step e) the phosphite triester resulting from step c) is oxidized to form the more stable phosphate triester, which process is often referred to as "oxidation". Oxidation is typically achieved using iodine reagents (such as for example iodine in THF/pyridine/water). In cases where phosphorothioate oligos are synthesized, the oxidation step e) may be replaced by a sulphurisation step.

In exemplary step f) the synthesis cycle including steps b) to e) is repeated as needed depending on the desired length of the oligonucleotide. The skilled in the art will recognize that in certain embodiments of the invention the order of steps may vary or some of the steps including the washing steps may be repeated as appropriate according to the used protocol. For example, after final step e) another step b) may be performed to remove the 5'-DMT group from the last coupled phosphoramidite. During synthesis, steps b) to e) may be carried out under positive gas pressure e.g. using argon or nitrogen or any other inert gas to prevent exposure of the reactive intermediates to air.

After synthesis, the oligonucleotides may be subject to exemplary step g) which includes cleavage of the oligonucleotides from the solid support and removal of the protecting groups, a process often referred to as "cleavage and deprotection". This is typically achieved using aqueous or gaseous ammonia at elevated temperatures. Both reactions may be performed subsequently or in a single step depending on the used conditions. For example, where gaseous anhydrous ammonia is used, both steps occur simultaneously and the fully deprotected oligonucleotide is eluted from the support either with water or buffer, depending on subsequent steps for quantification or purification. Deprotection conditions may also vary depending on the type of modification of the phosphoramidites used for synthesis or the type of nucleobase protection used to synthesize the oligonucleotide backbone. For example, standard DNA bases protected with conventional groups (e.g. Bz-dA, Bz-dC, iBu-dG) may be deprotected using ammonium hydroxide.

In some embodiments, it may be desired to leave the terminal 5'-DMT group on the synthesized oligonucleotides for subsequent purification by not performing a final deblocking step b). The trityl group can then be used to purify full-length oligonucleotides via hydrophobic interaction with C18 silica or polystyrene support. Alternatively or in addition, oligonucleotides may be purified by conventional methods such as desalting, reverse phase HPLC, polyacrylamide gel electrophoresis ("PAGE") or anion exchange HPLC.

Nucleic acids as used herein may comprise one or more reactive groups capable of reacting with an appropriate reactive group provided by another entity. For example, nucleic acids may further be modified with one or more reactive groups to allow subsequent labelling (e.g. with dyes, biotin, alkaline phosphatase etc.) or coupling to a functionalized surface. Such chemical modification can be provided during or after oligonucleotide synthesis. A wide variety of modifications are available to be incorporated into the oligonucleotide at the time of synthesis. This can be achieved by using a modified synthesis support, e.g. a modified CPG support suitable for 3' modifications, or an amino-modified phosphoramidite for internal and 5' modifications. The choice of modification type and position largely depends on the subsequent application or intended use.

In various embodiments, nucleic acids are provided with a reactive amine function for subsequent coupling reactions. In some embodiments a reactive amine function is added to the oligonucleotide after synthesis. In some embodiments a reactive amine is added to the oligonucleotide during synthesis. In some embodiments a reactive amine function is added to the 5' end of the oligonucleotide which is in many instances the target end for modification because of the ease of incorporation during the last step of automated synthesis. In other embodiments a reactive amine function is added to the 3' end of the oligonucleotide.

The reactive amine function can encompass in particular primary amines. A primary amine is typically represented by the formula "R—$NH_2$" and is distinct from an aromatic amine provided by the purine or pyrimidine rings of nucleotides, where the amine function is directly bonded to an aromatic group. The $NH_2$ group in a primary amine molecule is called the primary amine group. According to various embodiments, a nucleic acid can comprise a reactive amine function at its 3' or 5' terminus, which means that the reactive amine function is coupled to the nucleotide part of said nucleic acid. In other words, the at least primary amine function may be located at the 5' end or at the 3' end of the nucleic acid molecule. Amino groups introduced at the 5' end of a nucleic acid (e.g. using the one-step reaction method described by Chu and Orgel (DNA 4, 327-331, 1985), results in a greater nucleophilicity of the terminal primary amino group of the alkyl linker as compared to the amino functionalities of the bases. It is therefore expected that the carboxylic acid groups exposed on a support would react preferentially with these primary amino groups. A nucleic acid can comprise a reactive amine function "on the side" of its 3' or 5' terminus, which means that said amine function is not directly coupled to the nucleotide part of the nucleic acid, but is covalently bonded to a non-nucleotide part of said nucleic acid. Said non-nucleotide part is preferably bonded to the polynucleotide. The term "non-nucleotide part" is intended to mean a chemical unit which does not consist essentially of a polynucleotide.

A non-nucleotide part of a nucleic acid may for example be a non-nucleotide spacer chain which is interposed between said reactive amine function and said terminus of the nucleotide part of said nucleic acid. If bonded to the 3' or 5' terminus of the oligonucleotide, the spacer chain may serve as an "amine-modifier" (as described in more detail below) to incorporate a functional amine group into the nucleic acid. Thus, a reactive amine function can be attached to a 3' or 5' terminus of the nucleotide part of the nucleic acid or the spacer chain. A spacer chain may physically distance the nucleic acid from the surface of the support, thereby increasing the relative mobility of the nucleotide part of the nucleic acid for subsequent binding reactions and reducing its steric hindrance. Thus, in certain embodiments, the reactive amine function and the 5'- or 3'-end of the oligonucleotide are separated by a spacer chain.

The spacer chain may be of any type. The spacer chain essentially contains bonds of carbon-carbon, carbon-oxygen and carbon-nitrogen type. For example, a spacer chain may be a hydrophobic chain consisting of a chain composed of 3, 6, 12 or more (for example 18) methylenes ($CH_2$), also often referred to as C3, C6 or C12, respectively, or a hydrophilic chain which can be of polyethylene glycol type, for example hexaethylene glycol (HEG), or an 11-amino-3,6,9-trioxaundecan-1-yl, subsequently referred to as hydrophilic C11, or a nonspecific oligonucleotide, optionally substituted with a primary amine function. Preferably, the spacer chain does not comprise ionizable groups other than primary amine functions or secondary amine functions. Generally, the spacer chain does not comprise groups or bonds sensitive to alkaline pH or to oxidation or reduction reactions. In particular, the spacer chain does not contain any disulfide bond or thiol groups.

Figure 2:
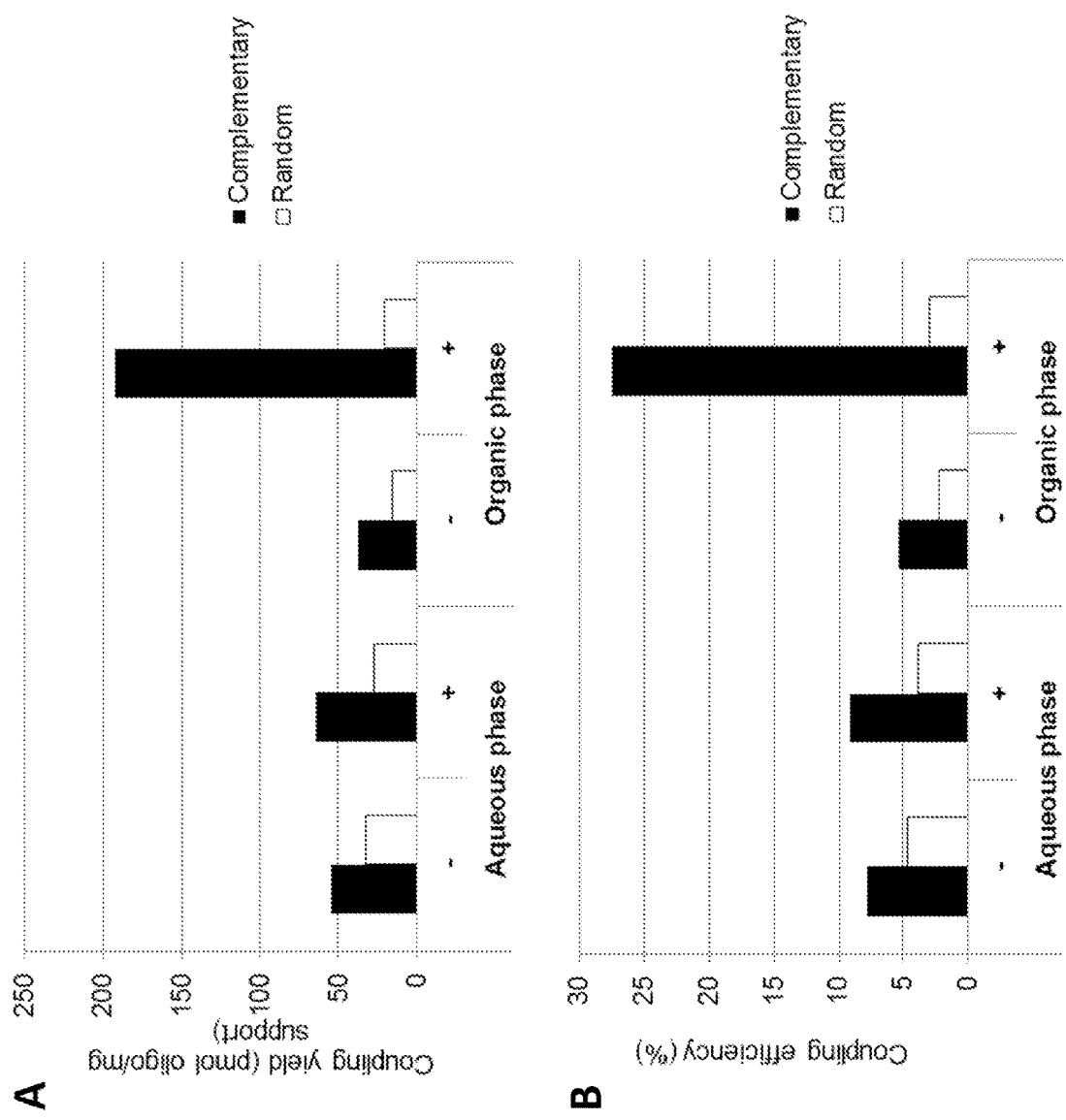
FIG. 2 shows a comparison of coupling yields (A) and coupling efficiency (B) obtained when using a standard process for coupling oligonucleotides to Dynabeads™ M-270 Carboxylic Acid functionalized support in aqueous phase (left panel) or in the presence of an organic solvent (right panel) according to various embodiments.

The spacer chain can be introduced according to methods well known to those skilled in the art, in particular as a final step of the chemical synthesis of the polynucleotide. In this particular case, the spacer chain may be introduced at the 5' end of the polynucleotide by means of a derivative comprising a phosphoramidite function. The general principle of this reaction is shown in FIG. 2 of Greco and Tor (Nature Protocols 2, 305-316, 2007). It is also possible to introduce a molecule containing a primary amine in the 5' position of the polynucleotide by coupling a diamine such as ethylenediamine in the presence of EDC (1-Ethyl-3-(3-dimethylaminopropyl)carbodiimide) and of imidazole (see technical sheet No. TR0030.5 published by Thermo Fisher Scientific). Reference may also be made to the reference manual by Hermanson (Bioconjugate Techniques, 2nd Edition, Academic Press, San Diego, 2008) and in particular to chapter 27, page 970.

A reactive amine function such as primary amino group can be attached to a nucleic acid using a so-called "amino-modifier". Amino-modifiers can have different chemistry and length. For example amino-modifiers for bases dA, dC, dG and dT are available and can be added in the last synthesis cycle instead of the respective regular base. Amino-modifiers may have spacer arms of various chemistry and length (including C3, C6, C12 methylene ($CH_2$) or longer) to provide flexibility in view of downstream applications where factors such as steric hindrance, electrostatic repulsion, binding kinetics, charge density, hydrophobicity and/or hybridization efficiency etc. are critical. For example, where oligonucleotides are attached to a support for use in a hybridization assay (e.g. a DNA array) the length, charge and hydrophobicity of the spacer arm linking the oligonucleotide to the support may significantly influence the efficiency of hybridization with a target nucleic acid (Shchepinov et al., Nucleic Acids Res. 25, p. 1155, 1997). In many instances C6 amino modifiers having a primary amino group at the end of a six-carbon spacer are used for standard 5' labeling. For certain applications also modifiers with longer spacer chains (such as e.g. C12) can be used. For 3' labeling amino modifier C7 or C3 are often used, which contain a branched seven-carbon or three-carbon spacer, respectively. Internal amino functions can be introduced to oligonucleotide sequences by a number of amino modifiers including C6-dA, C6-dC, C6-dG and C6-dT, and can be added in place of a dA, dC, dG and dT residue, respectively.

Amino-modifiers of various chemistry and length for 5' and/or 3' modification of nucleic acids are available from commercial suppliers such as e.g. Sigma-Aldrich™ (see e.g. "Custom Oligonucleotide Modifications Guide", Sigma-Aldrich), Link Technologies Ltd., Glen Research, Integrated DNA Technologies, Exiqon, etc. One example of an amino-modifier that is widely used in automated DNA synthesizers is Uni-Link™ AminoModifier (Clontech Laboratories, Inc.) which is a cyanoethyl phosphoramidite that directly incorporates primary aliphatic amines into nucleic acid molecules.

A primary amino group can be used to conjugate a variety of labels, dyes or other functionalities to the nucleic acid. For example, an oligonucleotide carrying a primary amino group can be reacted with a label or other molecule activated with an N-hydroxysuccinimide (NHS, $C_4H_5NO_3$) ester (e.g. a biotin-XX-NHS ester) or an isothiocyanate (e.g. fluorescein isothiocyanate, FITC). However, a label can also be attached through other functional groups.

Thus, in some embodiments, an oligonucleotide, primer, probe, ligand or aptamer includes a detectable moiety or label. The label can generate, or cause to generate, a detectable signal. In some embodiments, the detectable signal can be generated from a chemical or physical change (e.g., heat, light, electrical, pH, salt concentration, enzymatic activity, or proximity events). In some embodiments, the label can include compounds that are luminescent, photoluminescent, electroluminescent, bioluminescent, chemiluminescent, fluorescent, phosphorescent or electrochemical. In some embodiments, the label can include compounds that are fluorophores, chromophores, radioisotopes, haptens, affinity tags, atoms or enzymes. In some embodiments, the label comprises a moiety not typically present in naturally occurring nucleotides. For example, the label can include fluorescent, luminescent or radioactive moieties. Many ways of labelling nucleic acids are known by the skilled person. For example, WO 2014/095952 A1 discloses methods of making a labeled oligonucleotide for use as a hybridization probe.

Alternatively, the terminal amino group can be used to couple the nucleic acid to a functionalized surface such as a carboxylate modified support.

The term "solid support", "support", "solid surface", "surface" or similar terms as used herein refers to a material or substrate on which nucleic acids (including oligonucleotides, primers, probes etc. as discussed above) can be synthesized, attached and/or immobilized. The support can have any one of a number of shapes, such as pin, strip, plate, chip, disk, rod, fiber, bends, cylindrical structure, planar surface, concave or convex surface or a capillary or column or may be spherical, particulate, oval, polygonal and the like. The support or surface may be two-dimensional (such as a slide) or three dimensional such as beads or spheres. The support or surface can be a particle, including bead, microparticles, nanoparticles and the like. For example, the support may comprise a polymeric particle such as a polystyrene particle or may have a gel-like structure. In some embodiments the support may be a magnetic particle, bead or sphere. The solid support can be a non-bead type particle (e.g., a filament) of similar size. The support may be an array or chip, a glass slide etc. or a structure thereof. In many instances the support is selected from the group consisting of particles, spheres, microparticles, nanoparticles or beads.

The support or surface thereof can be hydrophilic or capable of being rendered hydrophilic and includes inorganic powders such as silica, magnesium sulfate, and alumina; natural polymeric materials, particularly cellulosic materials and materials derived from cellulose, such as fiber containing papers such as filter paper, chromatographic paper or the like. The support or surface can be immobilized at an addressable position of a carrier such as a multiwell plate, a slide or a microchip. The support can be loose (such as, e.g., a resin material in a vial or column or a bead/particle in a well) or can be reversibly immobilized or linked to the carrier (e.g. by cleavable chemical bonds or magnetic forces etc.). In some embodiments, solid support may be fragmentable. The solid support may be synthetic or modified naturally occurring polymers, such as nitrocellulose, carbon, cellulose acetate, polyvinyl chloride, polyacrylamide, cross linked dextran, agarose, polyacrylate, polyethylene, polypropylene, poly(4-methylbutene), polystyrene, polymethacrylate, poly(ethylene terephthalate), nylon, poly(vinyl butyrate), polyvinylidene difluoride (PVDF) membrane, glass, controlled pore glass, magnetic controlled pore glass, magnetic or non-magnetic beads, ceramics, metals, and the like; either used by themselves or in conjunction with other materials. A solid support as used herein may comprise solid as well as semi-solid material such as a hydrogel.

The support can have variable widths and sizes. For example, sizes of a particle or bead (e.g., a magnetic bead) which may be used in the practice of aspects of the invention may vary widely but include beads with diameters between 0.01 µm and 100 µm, 0.005 µm and 100 µm, 0.005 µm and 10 µm, 0.01 µm and 100 µm, 0.01 µm and 1,000 µm, between 1.0 µm and 2.0 µm, between 1.0 µm and 100 µm, 15 between 2.0 µm and 100 µm, between 3.0 µm and 100 µm, between 0.5 µm and 50 µm, between 0.5 µm and 20 µm, between 1.0 µm and 10 µm, between 1.0 µm and 20 µm, between 1.0 µm and 30 µm, between 10 µm and 40 µm, between 10 µm and 60 µm, between 10 µm and 80 µm, or between 0.5 µm and 10 µm.

Solid supports comprising particles or beads according to various aspects may be monodisperse. The term "monodisperse" means that for a plurality of particles (e.g. at least 100, more preferably at least 1,000) the particles have a coefficient of variation (CV) or % polydispersity of their diameters of less than 20%, for example less than 15%, typically of less than 10% and optionally of less than 8%, e.g. less than 5%. The term monodisperse is used herein to characterize a population of particles or particles with low heterogeneity and a homogenous size distribution. The size distribution of a particle may be defined by the percentage CV (coefficient of variation) which may be determined on a CPS disc centrifuge. CV is defined as 100 times (standard deviation) divided by average where "average" is mean particle diameter and standard deviation is standard deviation in particle size. The CV for a plurality of particles may for example be within a range of 50 to 100%. For example, a monodisperse particle population may have more than 90%, preferably more than 95% of the particles with sizes within their mean diameter of ±5%.

Monodisperse particles or beads were shown to provide certain advantages in magnetic separation assays. For example, by using monodisperse particles, the reaction rate and other parameters are particularly uniform. In particular, particles that are monodisperse and superparamagnetic greatly assist the kinetics of reactions in which the particles are involved. By using superparamagnetic particles or beads (i.e. particles containing sub-particles of ferromagnetic material which are smaller than the domain size required to maintain permanent magnetism), one can avoid magnetic aggregation or clumping of the particles during reaction, thus again ensuring uniform and rapid reaction kinetics.

Thus, methods and compositions of the invention may provide solid supports that are monodisperse and/or superparamagnetic. Such particles are described for example in U.S. Pat. No. 5,512,439.

The support can have a smooth or granular surface, and may be compact or porous. The term surface may also be used herein to describe the layer or part of a support that is exposed to or accessible by a solvent such as e.g. the pores of a porous material. As used herein, the term "porous" means that the material or particle contains pores which may be of non-uniform or uniform diameters (for example in the nm range). Porous materials in general include synthetic filters, resin, beads, membranes etc. In such porous materials, a reaction (e.g. in situ synthesis or attachment of molecules) may take place within the pores.

Thus, a support according to various embodiments may be porous. For example, porous particulate supports such as beads may be characterized by a specific pore volume, wherein, for example, 1 ml of pore volume per 1 gram of polymer is equal to 50% porosity. For example, a particle with a pore volume of 2.2 ml/g polymer has a porosity of 70%. Particle porosity depends on the polymer used. In certain instances the pore volume of a particle suitable for aspects of the invention may be within a range of 0.1 to 2.5 ml/g polymer. In some examples the particle has a pore volume of between about 1.0 and about 2.0 ml/g of polymer. However, porosities may also be defined on a volume basis. Particle porosities that may be useful for the disclosed methods and compositions may be within a range of from about 50% to about 70%, from about 55% to about 65%, such as e.g. about 60%. In some instances particles having a porosity of up to 99% may be used. Advantages of using porous bead-based platforms in diagnostic applications such as point-of-care tests have been reviewed by Chou et al. (Sensors. 12, 15467-15499, 2012).

In some instances, the use of a non-porous ("compact") support or material with smaller pores may be preferred. For example, less porous particles may have porosities within a range of from about 1% to about 10%, from about 2% to about 20% or from about 5% to about 50%. In some aspects, particles may have a regular or "smooth" structure. Smooth particles provide a uniform magnetic signal in all directions, unlike irregular particles. This provides for a more consistent performance when exposed to a magnetic field. A further advantage of smooth particles is that all of the outer surface is readily accessible, e.g. to a solution.

Surfaces suitable for attaching or conjugating molecules are often provided in a functionalized form. A support can be functionalized or coated or modified with various reactive groups. For example, ligands may be spotted onto an activated glass surface or other carrier, such as one coated with aminosilane, poly-lysine, aldehyde, epoxy or active esters (see e.g. Zammatteo et al., Anal. Biochem. 280, 143-50, 2000). One type of functionalized surface that is often used for covalent attachment of peptides or nucleic acids is carboxylated substrate, i.e. a surface coated with carboxylic acid groups. According to various embodiments, the support is modified with carboxylic acid groups to allow coupling to molecules carrying a reactive amine function. In some embodiments the carboxylic acid groups are directly attached to the support. In some embodiments the carboxylic acid groups directly extend from the support surface, i.e. without any spacer or crosslinker or other chemical moiety that attaches the carboxylic acid groups to the support. In some embodiments the carboxylic acid groups are introduced by coating the support with a polymer that carries carboxylic acid groups.

In various embodiments, the carboxylic acid groups may be activated prior to a coupling reaction. The term "activated carboxylic acid group" as used herein is intended to mean a chemical function derived from the "carboxylic acid" function capable of reacting with a nucleophile, in particular a primary amine so as to form an amide bond. Activated carboxylic acid functions are well known to those skilled in the art and encompass acid chloride, mixed anhydride and ester functions. The activated carboxylic acid functions may, for example be in the form of esters resulting from the reaction of said carboxylic acid functions with a compound chosen from the group constituted by 1-hydroxybenzotriazole (HOBt), HOAt and N-hydroxysuccinimide, or a derivative thereof. In some embodiments the activated carboxylic acid function is not derived from an activated poly(acrylic acid) attached to the support surface.

Selection of a suitable functionalized support for nucleic acid coupling according to various embodiments may depend on various parameters and should be compatible with downstream applications. For example, a major problem in using magnetic beads for fluorescence immunoassays is that the bead's autofluorescence strongly interferes with the target detection signal. Thus, where a nucleic acid-loaded support will be used in an assay that uses fluorescence read out based on labelled probes, a support composed of or coated with a material that comprises no or limited inherent autofluorescence may be preferred to reduce the level of scattering or fluorescence background. Various supports comprising low autofluorescence properties are described in the art including slides, microplates or polymer particles. For example autofluorescence of polymer particles may be reduced or avoided by keeping the particle essentially free of conjugated delocalized electron systems, other than those in benzene rings, as described in WO 2004/053490 A1. Such particles will not be cross-linked with divinylbenzene, since any unreacted compound will autofluoresce. Furthermore, when using particles in a fluorescent assay, the background signals derived from autofluorescent particles may be further limited by selecting particles of smaller size (e.g. smaller than or up to about 1 µm), such as the sub-micron beads described e.g. in U.S. publication No. 2012/0141798 A1 incorporated by reference herein.

In some instances, a fluorescent support may be used. For example, fluorescent micro-particles have been used in highly multiplexed liquid array applications and are available from various suppliers including Thermo Fisher Scientific and Applied BioCode. Such platforms use beads uniquely labeled with different fluorescent dye combinations and loaded with nucleic acids (oligonucleotides, probes etc.) that can hybridize to a labeled target ligand (other nucleic acids or peptides) in solution. Following specific hybridization to the target the combined fluorescent signals derived from such "barcoded" particles and the bound labeled target can be determined e.g. by flow cytometry. The use of barcoded beads loaded with nucleic acids for liquid array applications is described e.g. in Yang et al. (Genome Research 11, 1888-1898, 2001), or in Defoort et al. (J. Clin. Microbiol. 38, 1066-1071, 2000). Fluorescent particles that may be used according to various embodiments include in particular those that are functionalized with carboxylic acid groups. For example, Carboxylate-modified FluoSpheres™ (Thermo Fisher Scientific) have a high density of carboxylic acids on their surfaces and may be used for coupling of aminated nucleic acids according to the methods described herein.

General considerations for choosing an appropriate support may include the loading capacity of the support, which may depend on one or more of the following features: structure, size, surface area, porosity, surface chemistry, size of the specific molecules to be immobilized and the like. Whereas a very low loading capacity may lead to a low signal in a subsequent assay thereby affecting the assay sensitivity, a too high loading capacity may lead to high background signals or steric hindrance effects during nucleic acid coupling, which may compromise subsequent binding of a target molecule due to limited accessibility of the coupled nucleic acids. Thus, for some applications a support with very high loading capacity may be used, whereas for other applications a support with low and controlled loading capacity may be preferred. The effect of nucleic acid surface density on hybridization efficiency has for example been investigated by Guo et al. (Nucleic Acids Res., 22, 5456-5465, 1994) who determined the optimal surface coverage at which a maximum amount of a complementary target nucleic acid could be bound. Strategies in the preparation of oligonucleotide arrays for diagnostic applications are discussed, for example, in Beaucage, S. L. (Curr. Med. Chem., 8, 1213-44, 2001).

The loading density of a functionalized support is limited by the amount of reactive groups on the support surface that are accessible for coupling reactions. Whereas two-dimensional supports such as plates, slides or chips may be appropriate for specific applications, their planar structure limits the availability of reactive groups and thus, the maximum nucleic acid loading capacity. Thus, in many instances a suitable carboxylic acid-functionalized support may have a three-dimensional or particulate structure, such as a sphere, microparticle or beads.

Particulate supports typically have a higher loading capacity due to a larger surface to volume ratio, in particular when composed of porous material. Thus, a support according to various embodiments may be defined by its surface area. In many instances, porous particulate supports with a high surface area may be used. In particular small diameter particles present more surface area per unit weight, while larger particles present more surface area per particle. The surface area of porous polymer particles can, for example, be determined according to a method developed by Brunauer, Emmett and Teller referred to as the BET method which is based on the physical adsorption of a vapour or gas onto the surface of a solid (Brunauer, S., Emmett, P. and Teller, E., J. Amer. Chem. Soc. 60, 309-319, 1938). This method uses dry particles for testing so, for accurate measurement, the pores should be of stable volume when exposed to solvents as compared to when dry. In some embodiments, the particle surface area according to various embodiments may be within a range of about 10 to about 1,000 $m^2/g$, between about 100 and about 700 $m^2/g$, between about 200 and about 600 $m^2/g$, between about 300 and about 400 $m^2/g$, such as e.g. about 350 $m^2/g$. In some embodiments, particles may have a specific surface area within a range of about 2 to about 100 $m^2/g$, about 5 to about 50 $m^2/g$ or about 2 to about 5 $m^2/g$.

In some embodiments magnetic beads with high loading capacity may be used as solid support. For example, magnetic beads are often used in applications that comprise affinity separation, target purification or hybridization steps. Magnetic beads with carboxylic acid coated surface are commercially available from various vendors including Dynabeads™ M-270 Carboxylic Acid and Dynabeads™ MyOne™ Carboxylic Acid (Thermo Fisher Scientific), BioMag® Carboxyl (Bangs Laboratories Inc.), Sera-Mag™ Magnetic carboxylate modified particles (GE Healthcare), Estapor® Super Paramagnetic Microspheres (Merck Chimie SAS), ProMag™ 1 Series COOH Surfactant-Free Microspheres (PolySciences Inc.), Absolute Mag™ Carboxyl Magnetic Particles (Ademtech), Magnosphere™ MS160/Carboxyl particles (JSR Life Sciences), Mono Mag Carboxylic Acid Beads (Ocean Nanotech), or MagPlex® Microspheres (Luminex), etc.

Covalent linkage of amino-modified or aminated nucleic acids to a solid support require an acylating agent that forms carboxamides, sulfonamides, ureas or thioureas upon reaction with the amine. Prior to coupling of a nucleic acid, a support functionalized with carboxylic acid groups is typically activated with water soluble 1-ethyl-3-[3-dimethylaminopropyl] carbodiimide hydrochloride (also known as EDC, EDAC, EDC hydrochloride, WSC hydrochloride and alternatively written as N-Ethyl-N'-(3-dimethylaminopropyl) carbodiimide hydrochloride). Carbodiimides (RN=C=NR) and derivatives thereof are available from various vendors including e.g. Thermo Fisher Scientific Pierce. A typical coupling procedure with carbodiimide chemistry is illustrated in FIG. 1. In step (1), a carboxylate-modified support (represented by a black sphere) is activated with carbodiimide EDC to form a reactive anhydride or O-acylisourea (i.e. an O-acylated derivative of urea). In step (2), the highly reactive intermediate which seeks to eliminate the urea unit reacts with the primary amine functional group of an aminated oligonucleotide to form a stable carbonyl amide bond, with isourea being released as a by-product. This procedure can be used to couple amino-modified oligonucleotides to an activated carboxylated surface via the 5' or 3' end depending on where the primary amino group is present.

In methods known in the art, the activation in step (1) and the coupling reaction in step (2) are typically conducted in aqueous phase. Activation of carboxylic acid groups with EDC has been shown to be efficient at a pH between 4.5 and 7.2. Therefore, many available protocols suggest using a MES (2-morpholinoethanesulfonic acid) buffer with a pH of about 5 or 6 or an imidazole buffer at pH 7.0 for the activation and coupling reaction (Nakajima and Ikada, Bioconjugate Chemistry, 6, pp. 123, 1995). In principle, the buffer should be free of any compounds that interfere or compete with the reaction. For example, phosphate and acetate buffers can reduce the reactivity of carbodiimides, and are thus not recommended for coupling to carboxylated support. Furthermore, when using amine-reactive reagents it is critical that during the coupling step, buffers are used that do not contain any free amines (such as Tris or glycine) which could interfere with the coupling reaction.

The inventors have surprisingly found that the yield of aminated oligonucleotides immobilized on carboxylated support can be significantly increased when both, the activation and coupling reactions in steps (1) and (2) are performed in a solution comprising an organic solvent.

Therefore, according to various embodiments, the invention provides a method for coupling a nucleic acid to a support comprising:
  (a) providing a support comprising thereon carboxylic acid groups,
  (b) providing a nucleic acid, wherein the nucleic acid comprises at least one primary amine function,
  (c) activating the support by contacting the carboxylic acid groups thereon with a carbodiimide or a derivative thereof, to form a reactive anhydride,
  (d) reacting the reactive anhydride on said activated support with the at least one primary amine function of the nucleic acid to form a covalent amide bond, thereby coupling said nucleic acid to the support,
  wherein steps (c) and (d) are conducted in the presence of an organic solvent.

Figure 3:
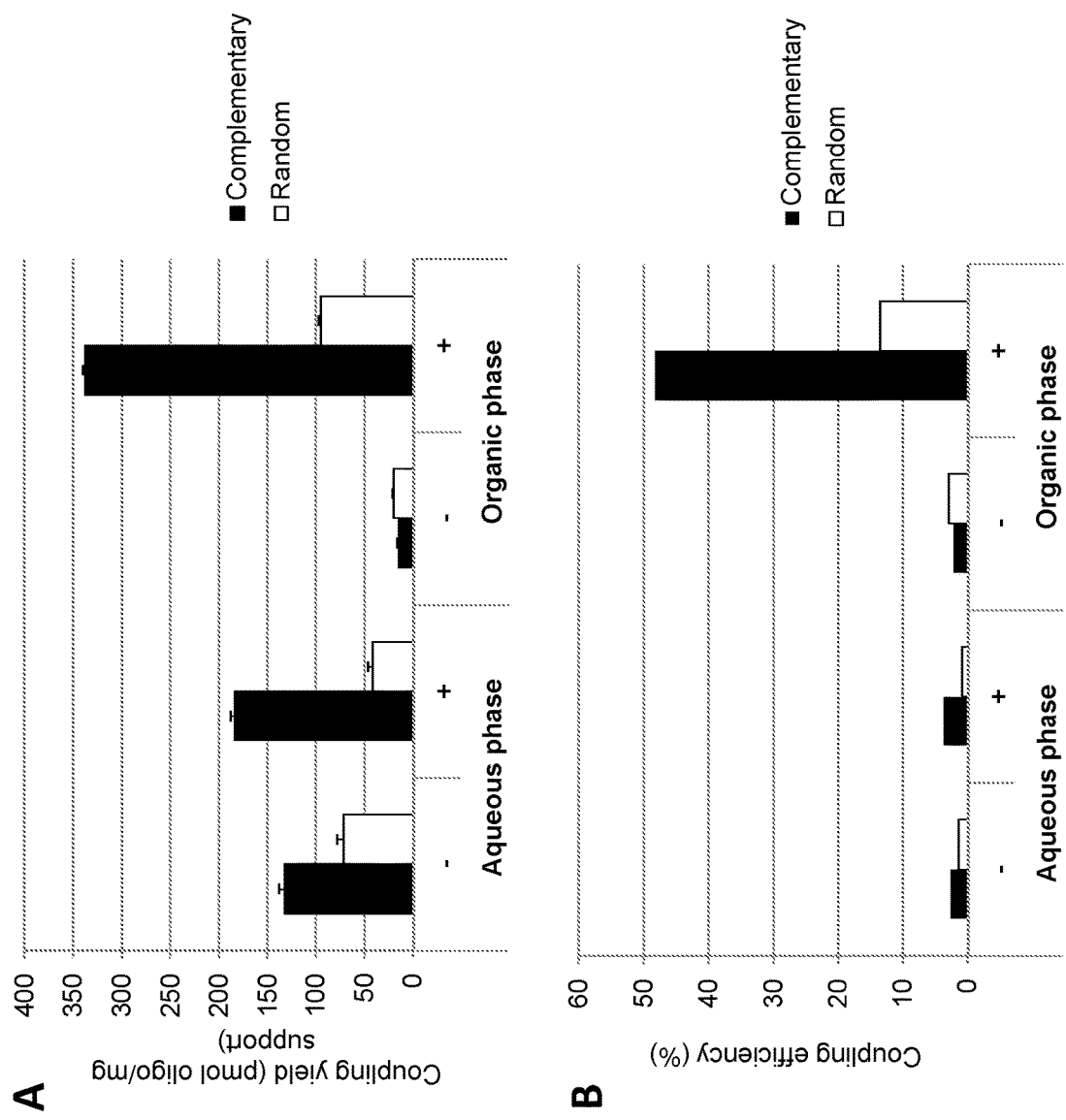
FIG. 3 shows a comparison of coupling yields (A) and coupling efficiency (B) obtained when using a standard process for coupling oligonucleotides to Dynabeads™ MyOne Carboxylic Acid functionalized support in aqueous phase (left panel) or in the presence of an organic solvent (right panel).

As supported by the data described in Example 1 and illustrated in FIGS. 2 and 3, this improved procedure resulted in up to about three times increased yield of nucleic acid coupled to an exemplary carboxylic acid functionalized support as compared to a standard method where the activation and coupling reactions were performed in aqueous phase. Furthermore, it has been observed that non-specific coupling events were reduced in the presence of organic solvent. (FIGS. 2A and 3A). Without wishing to be bound by any theory, the applicant believes that the low polarity of organic solvent (as compared to water) affects the folding properties or conformation of the nucleic acids and reduces the amount of secondary structures which may provide better accessibility of the primary amino group attached to the nucleic acid for interaction with the activated support. Secondly, without wishing to be bound by any theory, if present, an aliphatic spacer chain of an aminated nucleic acid may become more exposed through interaction with the aprotic solvent. Thirdly, the organic solvent prevents the O-acylisourea intermediate (which is unstable in aqueous solvent) from hydrolysis to keep the carboxylic acid groups in an activated state thereby favoring the coupling of the aminated nucleic acids to the functionalized support. In sum, one or more of these effects may contribute to (i) higher overall coupling rates and (ii) preferred coupling of nucleic acids via their primary amine function as compared to non-specific coupling to the amino functionalities of the bases. Also, due to the increased coupling efficiency, less nucleic acid is required for efficient coupling (FIGS. 2B and 3B).

The organic solvent according to various embodiments is miscible with water. In some instances, the organic solvent may be hydrophobic. In some embodiments, the organic solvent may be an aprotic polarity solvent. The organic solvent may be selected from the group consisting of dimethyl sulfoxide (DMSO, $C_2H_6SO$), dimethylformamide (DMF, $C_3H_7NO$), tetramethylurea, methanol, ethanol, isopropanol, ethylene glycol, acetone ($C_3H_6O$), an aprotic glycol diether such as bis(2-methoxyethyl)ether (also referred to as diglyme) or (bis(methoxypropyl)ether (also referred to as Proglyde™), acetamide, diethyl sulfoxide (DESO) or any mixtures thereof. In some embodiments the organic solvent may be dimethyl sulfoxide. DMSO is a non-toxic organic solvent and therefore particularly user-friendly.

In some embodiments the concentration of organic solvent present during the activating is at least about 30%, at least about 40%, at least about 50%, at least about 60%, at least about 70%, at least about 80% or at least about 90%. In some embodiments the concentration of organic solvent present during the activating is less than 100%. In some embodiments the concentration of organic solvent present during the activating is within a range of about 50% to about 100%, for example about 90%. In some embodiments the concentration of organic solvent present during the activating is at least about 50% and not more than about 95%, preferably not more than about 90%. In some embodiments the concentration of organic solvent present during the coupling is at least about 30%, at least about 40%, at least about 50%, at least about 60%, at least about 70%, at least about 80% or at least about 90%. In some embodiments the concentration of organic solvent present during the coupling is less than 100%. In some embodiments the concentration of organic solvent present during the coupling is within a range of about 50% to about 100%, for example about 90%.

In some embodiments the concentration of organic solvent present during the coupling is at least about 50% and not more than about 95%, preferably not more than about 90%. In some embodiments the concentration of water or aqueous components present during the activating and/or coupling is not more than 20%, preferably not more than 10%. Thus, in some embodiments, step (c) and/or step (d) of methods of the invention are conducted in the presence of water or an aqueous buffer, wherein the concentration of water or aqueous buffer is less than 20%, preferably less than 10% per total volume.

In some embodiments the activation and/or coupling is conducted in the presence of an organic solvent and water or aqueous components, wherein the ratio of organic solvent to water in the final reaction mixture is from between about 1:1 to about 9:1 (volume parts). In some embodiments, the ratio of organic solvent to water in the final reaction mixture is at least about 9:1. In some embodiments the water content of the activation and/or coupling solution may be adjusted in view of the length of the nucleic acid to be coupled, since longer nucleic acids may require a higher amount of water to remain soluble in organic solvent. For example, a shorter oligonucleotide of about 20 bases may be soluble in nearly anhydrous solutions containing only about 1% of water. In such instances, the water content of the activation and/or coupling solution may be at least 1%. Accordingly, the content of organic solvent in the activation and/or coupling solution may be at least about 90% and less than 100%. In some instances the required water content may depend on the specific organic solvent used.

Figure 5:
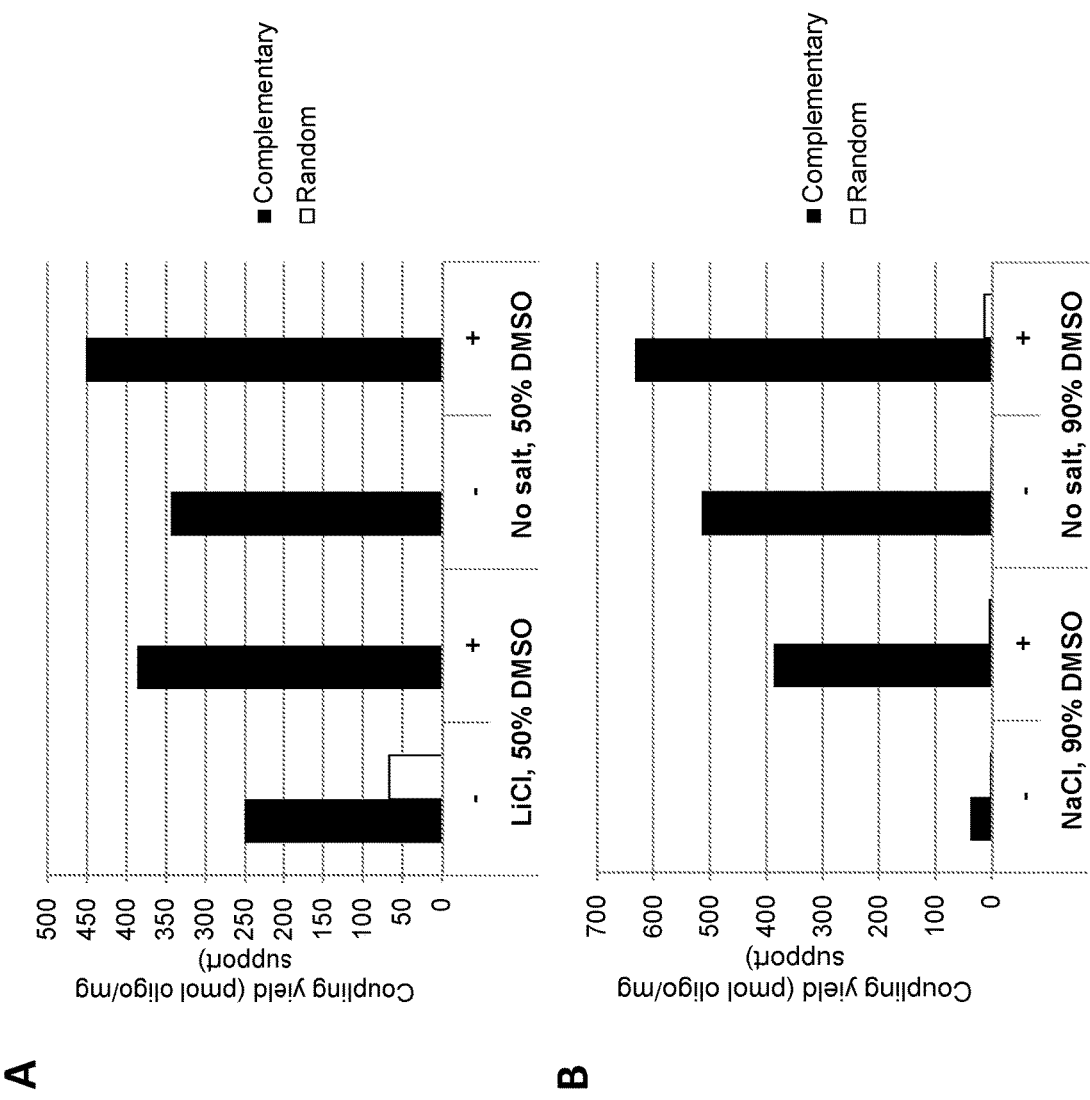
FIG. 5 shows the effect of the salts LiCl (A) and NaCl (B) on the coupling yield and non-specific binding of nucleic acid in organic solvent.

In a preferred embodiment, the activating step (c) and/or the coupling step (d) are conducted in the presence of a salt. The inventors have surprisingly found that in the absence of a salt more unspecific coupling (i.e. binding of nucleic acids to the support, where such binding is not mediated by a terminal reactive amine function) may occur, as described in Example 4 and and FIGS. 5 and 6, respectively. The addition of a salt to the reaction mixture may therefore increase the efficiency of specific nucleic acid coupling to the activated support. The salt is preferably highly soluble in organic solvent. The salt may be an inorganic or organic salt. In some embodiments the salt may be LiCl or NaCl. In some instances, the salt may not include an ammonium salt.

The optimal amount of salt present during the activation and/or coupling reaction may depend on various factors including solubility in the organic solvent, capability to precipitate nucleic acids etc. For example, the amount of salt may be sufficiently high to decrease unspecific coupling but may be sufficiently low to avoid precipitation or clumping of nucleic acids. In some embodiments the concentration of salt present during the activating is at least about 0.1 M. In some embodiments the concentration of salt present during the activating is less than about 1 M, or less than about 0.9 M. In some embodiments the concentration of salt present during the activating is within a preferred range of about 0.2 M to about 0.8 M, for example about 0.2 M, 0.3 M, 0.4 M, 0.5 M, 0.6 M, 0.7 M, 0.75 M or any value within the preferred range. In some embodiments the concentration of salt present during the activating is not less than about 0.2 M and not more than about 0.8 M. In some embodiments the concentration of salt present during the coupling is at least about 0.1 M. In some embodiments the concentration of salt present during the coupling is less than about 1 M, or less than about 0.9 M. In some embodiments the concentration of salt present during the coupling is within a preferred range of about 0.2 M to about 0.8 M, for example about 0.2 M, 0.3 M, 0.4 M, 0.5 M, 0.6 M, 0.7 M, 0.75 M or any value within the preferred range. In some embodiments the concentration of salt present during the coupling is not less than about 0.2 M and not more than about 0.8 M. In some embodiments the salt may be present at about equal concentration during the activating and the coupling. For example, the salt may be present during the activating and coupling at a concentration of about 0.75 M.

In some embodiments the amount of salt added to the reaction to support efficient coupling may depend on the organic solvent content of the reaction solution.

In some embodiments the salt may be dissolved in organic solvent prior to use in activating step (c), i.e. prior to contacting the salt with the support. For example, the salt may be dissolved in organic solvent (such as DMSO) prior to admixing the salt solution with the support and, optionally, the nucleic acid. In some embodiments the nucleic acid may be dissolved in organic solvent prior to use in activating step (c) and/or coupling step (d), i.e. prior to contacting the nucleic acid with the support. For example, the nucleic acid may be dissolved in organic solvent (such as DMSO) prior to mixing the nucleic acid solution with the support and, optionally, the salt. In some embodiments both the salt and the nucleic acid may be dissolved together in organic solvent prior to use in the activating and/or coupling.

In some embodiments the support may be dissolved in, mixed with, overlaid with or contacted with organic solvent prior to contacting the support with the salt and/or nucleic acid. In some embodiments the support is washed with NaOH and/or an appropriate buffer or water prior to the mixing or contacting with the organic solvent. For example, the support may be washed one or several times with an NaOH solution and optionally washed one or several times with "reverse osmosis" (RO) (i.e. purified, deionized) water. For the purpose of illustration, the support may for example be washed twice with a 10 mM NaOH solution and subsequently washed 2-4 times with RO-water. Different washing methods for functionalized supports are known that can be used to remove aqueous buffer or traces of water or other contaminants (such as RNAse etc.) which may otherwise interfere with the coupling reaction.

In some embodiments the carbodiimide or derivative thereof for activating the support may be a water soluble carbodiimide. In some instances, the carbodiimide may be 1-ethyl-3-[3-dimethylaminopropyl] carbodiimide which is also referred to as EDC, EDAC, EDCI, EDC hydrochloride, WSC hydrochloride or alternatively as N-Ethyl-N'-(3-dimethylaminopropyl) carbodiimide hydrochloride). In some instances the carbodiimide may be N,N'-dicyclohexylcarbodiimide also referred to as DCC. In other instances the carbodiimide may be N, N'-diisopropylcarbodiimide also referred to as DIC. In various aspects, a water soluble carbodiimide or derivate thereof is dissolved in aqueous buffer or water prior to use in the activating step. The aqueous buffer may for example be a 2-morpholinoethanesulfonic acid (synonyms include 2-(4-morpholino)ethanesulfonic acid; 2-(N-morpholino)ethanesulfonic acid MES hydrate; and morpholine-4-ethanesulfonic acid hydrate) buffer, widely known as "MES" buffer. In some instances, the aqueous buffer may have a pH of between about 4.5 and about 7. In some instances the aqueous buffer may have a pH of above 4.5 and below 7. In some instances, the aqueous buffer may have a pH of between about 5.0 and about 7. In some instances the aqueous buffer may have a pH of about, 5.0, 5.5, 6.0, 6.5, or 7. The carbodiimide or derivative thereof is preferably dissolved in an aqueous buffer immediately prior to use in the activation step (c). By way of illustration, it is also possible to use the methodology of activation by a combination of EDC and NHS. For example, water soluble sulfo-N-hydroxysuccinimide can be added to the activated support. The active ester intermediate formed by the N-hydroxy compound will replace the instable O-acylisourea intermediate formed by the carbodiimide, and is more stable to hydrolysis and yet still reactive for subsequent coupling reactions. In some embodiments, the carbodiimide or derivative thereof (such as DCC or DIC) is soluble in an organic solvent, and maybe dissolved in an organic solvent prior to use in the activating step.

In some embodiments the activating step (c) is performed at a pH of between about 4.5 and about 7.0. In some embodiments the activating step (c) is performed at a pH of between about 4.7 and about 6.7. In some embodiments the activating step (c) is performed at a pH above 4.5. In some embodiments the activating step (c) is performed at a pH below 7.0. In some embodiments the coupling step (d) is performed at a pH of between about 4.5 and about 7.0. In some embodiments the coupling step (d) is performed at a pH of between about 4.7 and about 6.7. In some embodiments the coupling step (d) is performed at a pH above 4.5. In some embodiments the coupling step (d) is performed at a pH below 7.0. In some embodiments, both the activating step (c) and coupling step (d) are performed at equal pH. In some embodiments the activating step (c) and coupling step (d) are performed at a pH of between about 4.7 and about 6.7. In some embodiments the activating step (c) and coupling step (d) are performed at a pH of about 6.7.

In some embodiments the activating step (c) is conducted at a temperature of between about 4° C. and about 30° C. In some embodiments the activating step (c) is conducted at a temperature of at least about 4° C. In some embodiments the activating step (c) is conducted at a temperature of less than 30° C. In some embodiments the activating step (c) is conducted at room temperature. In some embodiments the coupling step (d) is conducted at a temperature of between about 4° C. and about 30° C. In some embodiments the coupling step (d) is conducted at a temperature of at least about 4° C. In some embodiments the coupling step (d) is conducted at a temperature of less than 30° C. In some embodiments the coupling step (d) is conducted at room temperature. In some embodiments both the activating and coupling are conducted at room temperature. The term "room temperature" as used herein means the ambient temperature at typical laboratory conditions which is typically between about 20° C. to about 25° C. Room temperature (or "RT" as used in the examples) may therefore refer to a temperature range or to specific temperature values within that range, such as e.g. 20° C., 21° C. or 25° C. In certain instances, room temperature is equal to 25° C.

In some embodiments the activating is conducted independently from the coupling. This can be achieved by adding the nucleic acid to the support after the activation reaction is complete. In some embodiments the coupling is already initiated while the activating still proceeds. This can be achieved by mixing the nucleic acid and the carboxylate support before the carbodiimide is added. In instances, where the reactive intermediate is instable, it may be preferred to mix the nucleic acid and the support before the activation reaction is initiated by adding the carbodiimide or derivative thereof.

In some embodiments, the coupling reaction is allowed to occur for at least three hours, preferably at least six hours, more preferably at least 10 hours. In some embodiments the coupling reaction is allowed to occur for at least 14 to 18 hours to complete the coupling reaction.

In some embodiments, the coupling efficiency may be defined as the percentage of carboxylic acid groups on the support bonded via an amide bond to a nucleic acid. In some embodiments the coupling efficiency may be defined as the percentage of input nucleic acid provided during the coupling reaction that is covalently bound to the activated carboxylic acid groups on the support. For example, a solid support to which nucleic acids are coupled via an amide bond according to various embodiments may exhibit a nucleic acid density of about 50 to about 800 pmol/mg support. In some embodiments, the coupling efficiency is at least about 3%, at least about 5%, at least about 10%, at least about 20%, at least about 30%, or at least about 50%. In some instances the coupling efficiency may be between about 5% and about 20%, between about 10% and about 50%, between about 50% and about 90% such as for example about 50%, about 60%, about 70%, about 80% or about 90%.

The efficiency of coupling nucleic acids to a support can be determined by various means. For example, by measuring the change in absorbance of the coupling solution before and after the coupling reaction. One test that is often used to determine coupling efficiency of oligonucleotides on a solid support is the hybridization assay illustrated in FIG. 4. In a first coupling step (1.) of FIG. 4, an oligonucleotide (e.g. oligo(dT)$_{25}$) is coupled to a support (e.g. a bead represented by a black sphere). In a subsequent hybridization step (2.) the oligo-coated support is combined with either (a) a complementary oligonucleotide (in this example oligo (dA)$_{25}$), (b) a non-complementary oligonucleotide of random sequence and equal length, or (c) no oligonucleotide. After one or more washing steps (3.) hybridized oligonucleotides are eluted (4.) and the amount of eluted oligonucleotide from samples (a), (b) and (c) is measured to determine the amount of support-coupled oligo(dT)$_{25}$ (from sample a), the level of non-specific binding during hybridization (from sample b) and background signal (from sample c) for correction. Such hybridization assay can be used according to various embodiments to assess the suitability of nucleic acid-loaded support for use in a specific application. Other methods may also be used to determine the amount of nucleic acid immobilized on a solid support. For example, coupled nucleic acids may be hybridized with a dye-labeled probe or labeled with a dye that only becomes fluorescent upon binding to a nucleic acid molecule (e.g. a fluorophore such as Quant-iT™ OliGreen™) and measured signals (e.g. fluorescence intensity at a given wavelength) may be compared to a reference value, as described e.g. in WO 2017/100283 A1.

A method of the invention may further comprise a step (e) of separating the coupling solution of step (d) from the support and washing the support. The solution may be removed by any means known in the literature. For example, the solution may be removed by decanting, pipetting, suction etc. Where the support comprises magnetic material, the solution may be removed after the magnetic support has been immobilized on a magnet. Alternatively, the magnetic support may be removed from the solution by using a magnet, such as e.g. a magnetic pipette tip. After separation of the support from the coupling solution the support may be washed one or several times. Such washing may be performed with an aqueous solution, such as e.g. an aqueous buffer or water. The support comprising the coupled nucleic acids may then be stored in water or an appropriate buffer for further use depending on the downstream application.

The support comprising the coupled nucleic acids may further be treated to remove traces of contaminants that may interfere with downstream applications. For example, reagents, such as buffer components, organic solvent or salt may be removed by washing the support with a solution containing a detergent (such as e.g. Tris buffer comprising 0.1% Tween). Components having enzymatic activity (such as RNAse) may be removed or inactivated by adding a NaOH solution, either in a separate washing step or together with the detergent. Furthermore, the solid support comprising the coupled nucleic acids may be subjected to a heating step to remove or denature any nucleic acid that is non-specifically or non-covalently attached to the support (e.g. via binding or hybridization to a coupled nucleic acid molecule). Thus, washing and/or heating of the support may be useful for removing contaminants as well as non-specifically bound nucleic acid molecules. In addition, such treatment may resolve secondary structures and hairpins of coupled nucleic acids to increase the binding efficiency in subsequent hybridization based assays.

Thus, a method of the invention may further comprise a step of (f) washing and/or heating the support. In an exemplary embodiment step (f) may comprise contacting the support with a solution comprising NaOH and/or a detergent. The optional heating step may either be a separate step (performed prior to or after the washing) or may be performed during or combined with the washing step. For example the support may be heated to at least about 40° C., at least about 45° C., at least about 50° C., at least about 55° C., at least about 60° C., at least about 65° C. or at least about 70° C. In more general terms, the support may be heated to a temperature that reflects the specific melting temperature (Tm) of the coupled nucleic acid molecules. The support may be heated for at least about 2 min., at least about 5 min., at least about 10 min. or at least about 20 min.

The length of a nucleic acid (e.g. an oligonucleotide) that is to be coupled to a support according to various embodiments may vary depending on the structure/size or chemical properties of the support and/or the subsequent use of the loaded support. In some instances the oligonucleotide may have a length of at least about 5, 10, 15, 20 or 25 nucleotides. Where loaded supports are used in a hybridization assay, the length of the coupled nucleic acid should be sufficient to allow efficient hybridization of a complementary nucleic acid molecule. The terms "complementary" or "complementarity", as used herein, refer to the natural binding of nucleic acids (primers, probes, oligonucleotides etc.) under permissive salt and temperature conditions by base pairing. For example, the sequence "5'-A-G-T-3'" binds to the complementary sequence "3'-T-C-A-5'". Complementarity between two single stranded molecules may be "partial", such that only some of the nucleic acids bind, or it may be "complete", such that total complementarity exists between the single stranded molecules. The degree of complementarity between nucleic acids has significant effects on the efficiency and strength of the hybridization between the nucleic acid strands. This is of particular importance in hybridization reactions, which depend upon binding between nucleic acids strands. The longer the region of complementarity between the oligonucleotide and a target nucleic acid, the stronger is the interaction between them. However, oligonucleotides exceeding a certain length may stick together or form secondary structures thereby generating steric hindrance on the support, which may affect binding efficiency. Thus, the optimal length of a support-bound oligonucleotide for a hybridization or ligand binding assay may be between about 10 and 50 nucleotides, preferably between about 15 and 30 nucleotides. The optimal length of the nucleic acid may also be adjusted in light of the number or density of functional groups on the support to guarantee an optimal distribution of the nucleic acid molecules on the support. Furthermore, the length of a nucleic acid that can be efficiently coupled to a functionalized support may also depend on the solubility of the nucleic acid in the organic solvent. For example, a single stranded DNA oligonucleotide having up to 30 bases may be more soluble in certain organic solvents than an oligonucleotide having 50 or more bases.

The invention further provides a composition comprising:
  a support comprising thereon (activated) carboxylic acid groups,
  a nucleic acid comprising at least one primary amine function, and
  an organic solvent.

Such composition can be used for coupling the aminated nucleic acid to the carboxylate support at high efficiency.

The invention further provides a composition comprising:
  a support comprising thereon carboxylic acid groups, wherein at least a first portion of the carboxylic acid groups is modified with a reactive anhydride and at least a second portion of the carboxylic acid groups is bonded to a nucleic acid via a carbonyl-amide bond, an organic solvent, and optionally an isourea by-product.

The composition may further comprise a nucleic acid with at least one primary amine function in solution. The composition may further comprise a carbodiimide or derivative thereof.

The invention further provides a composition comprising:
  a support comprising thereon carboxylic acid groups bonded to a nucleic acid via a carbonyl-amide bond, and an organic solvent,
  wherein the support is beads having a nucleic acid coupling density of between about 40 and about 1,000 pmol/mg support, or between about 50 and about 800 pmol/mg support.

According to various embodiments, the composition may further comprise a salt. The salt may be of any type and concentration as described above in the context of the methods of the invention. The salt may for example be LiCl or NaCl and be present at a concentration of between about 0.2 and 0.8 M. The composition may have a pH of between about 4.5 and 8.0. In some embodiments the composition does not comprise a NHS compound. In some embodiments the composition does not comprise polyacrylic acid.

The amount of available functional groups for coupling depends on the type of support. In some instances, the initial density of carboxylic acid groups on a solid or semi-solid support may be between 5 µmol/ml and 25 µmol/ml of support.

For purpose of illustration the number of functional groups on a particulate support (e.g. beads) may be between about 100 and about 1,000 nmol/mg, such as e.g. between about 140 and 280 nmol/mg or between about 400 and 800 ng/mg. Based on the number of functional groups on such solid support, the number of carboxylic acid groups involved in a covalent binding with a nucleic acid molecule after coupling may vary between about 0.08 and 0.16%. Assuming that for example 5 nmol of nucleic acid would be added to the reaction, the coupling density may be between about 0.6 and about 3.6% depending on the type of support and the number of functional groups at the support surface.

Thus, according to the coupling process of the invention, it is possible to derivatize, at least 0.1% of the carboxylic functions initially present at the surface of the solid support, advantageously at least 0.2%, better still at least 1% and even better still at least 2% of said carboxylic acid groups.

In some embodiments the percentage of carboxylic acid groups on the support that are bonded to a nucleic acid via a carbonyl-amide bond is at least 0.1%, at least 0.5%, at least 5%, at least 10%, or at least 20%. The percentage of carboxylic acid groups that can be occupied with a nucleic acid molecule also depends on the amount or concentration of nucleic acid that would typically be used for a coupling reaction. For example, the concentration of nucleic acid during the coupling reaction may be within a range of about 10 to about 10,000 pmol/mg support or about 50 to about 5,000 pmol/mg support.

Furthermore, any embodiment or feature described above (alone or in combination) in the context of methods of the invention with respect to the support, the carbodiimide or derivative thereof, the nucleic acid, and the organic solvent does likewise apply to compositions of the invention.

A composition according to various embodiments may further comprise the organic solvent at a concentration of at least about 30%, at least about 40%, at least about 50%, at least about 60%, at least about 70%, at least about 80% or at least about 90%. In some embodiments the concentration of organic solvent in the composition is less than 100%. In some embodiments the concentration of organic solvent in the composition is within a range of about 50% to about 100%, for example about 90%. In some embodiments the concentration of organic solvent in the composition is at least about 50% and not more than about 95%, preferably not more than about 90%. In some embodiments, the content of organic solvent in the composition is at least about 90% and less than 100%. In some embodiments the composition comprises an organic solvent and water or an aqueous component. In some embodiments, the concentration of water or aqueous component in the composition is not more than 20%, preferably not more than 10%. In some embodiments the ratio of organic solvent to water in the composition is from between about 1:1 to about 9:1 (volume parts). In some embodiments, the ratio of organic solvent to water in the composition is at least about 9:1. In some embodiments the water content of the composition may be adjusted in view of the length of the nucleic acid to be coupled, since longer nucleic acids may require a higher amount of water to remain soluble in organic solvent. For example, where a nucleic acid of about 20 bases is present, the water content of the composition may be about 1%. In some instances the required water content may depend on the specific organic solvent used.

By way of illustration an exemplary composition may comprise (optionally magnetic) particles as solid support, wherein the particles are functionalized with carboxylic acid groups. The composition may further comprise a single stranded DNA oligonucleotide carrying a 5' or 3' primary amine function. The oligonucleotide may have a length of between about 15 and about 30 bases. The composition may further comprise DMSO as organic solvent. The composition may further comprise LiCl or NaCl as a salt at a concentration of between about 0.2 and 0.8 M. The composition may have a pH of between about 6.0 and 7.0. The composition may further comprise EDC for activating the carboxylic acid groups. The composition may further comprise a water content of up to about 10%.

The invention further provides a kit for coupling nucleic acid to a solid support comprising:
a support comprising thereon carboxylic acid groups,
an organic solvent,
a carbodiimide or derivative thereof,
and optionally a nucleic acid.

A kit according to various embodiments may further comprise a salt. The salt may be of any type and concentration as described above in the context of the methods and compositions of the invention. The salt may be provided as powder or in solution (e.g. in the form of a buffer). In some embodiments the kit may further comprise a nucleic acid. The nucleic acid may comprise at least one primary amine function or may be provided together with an amino modifier as outlined above. Nucleic acids provided with a kit or comprised in a composition according to various embodiments may further be labeled with any label described above. In some embodiments the kit may further comprise a buffer for dissolving the carbodiimide or derivative thereof. Such buffer may be an aqueous buffer, such as e.g. an MES buffer. The kit may further comprise a random oligonucleotide for use as control in a hybridization assay. In some embodiments the support may be magnetic particles or beads.

Furthermore, any embodiment described above in the context of the method and/or composition with respect to the support, the carbodiimide or derivative thereof, the nucleic acid, and the organic solvent can be likewise applied to kits of the invention. For example, kits of the invention can be used to couple aminated nucleic acids to a carboxylated support using any of the activating and coupling procedures described above.

The invention further relates to the use of methods, compositions and kits described herein for various applications. An increasing number of applications or in vitro assays are designed to allow specific capture of targets (such as nucleic acids or peptides) from various sample types with nucleic acids immobilized on solid supports. Nucleic acid-loaded supports described herein can be used for a variety of applications including microarray, hybridization assays, bio- and/or affinity separation, magnetic separation, for use in liquid arrays or as instrument standards, etc. For example, arrays of immobilized oligonucleotides obtained according to various embodiments may be used for sequencing by hybridization and array-based analysis of gene expression. In particular, oligonucleotide-based DNA microarrays are becoming increasingly useful tools for the analysis of gene expression and single nucleotide polymorphisms (SNPs). Furthermore, nucleic acid-loaded beads obtained by methods, compositions and kits of the invention may be used for ultra-high sensitivity applications such as bio-barcode assays as described e.g. in Hill and Mirkin (Nat. Protoc. 1, 324-36, 2006). Other applications include the capture or purification of mRNA (e.g. for subsequent therapeutic use). For example oligo(dT) may be coupled to a solid support such as beads using methods of the invention. The oligo(dT) support can then be used to specifically isolate polyadenylated mRNA molecules from a sample or mixture. The current invention will contribute to make such assays more sensitive and specific and thus more efficient.

EXAMPLES

Example 1: Coupling of amino-modified oligonucleotides to carboxylic acid beads

The coupling was conducted with Dynabeads™ M-270 Carboxylic Acid and Dynabeads™ MyOne™ Carboxylic Acid from Thermo Fisher Scientific. The beads were suspended thoroughly in the vials and a volume corresponding to 1 mg of beads each were transferred to 0.5 mL tubes. The beads were washed twice with 100 μL of 10 mM NaOH and incubated for 5 minutes with good mixing. The beads were immobilized to a DynaMag™-2 magnet (Thermo Fisher Scientific) for 2 minutes and the supernatant was removed. The beads were washed four times with RO-water and with DMSO (Sigma Aldrich) before applying the beads to the magnet for 2 minutes and removing the supernatant. 18.2 μL of 0.75 M LiCl dissolved in DMSO, and 71.1 μL of DMSO were added to the bead samples and each sample was provided with 0.7 μL (1 nmol/μL) of either 5'amino C6-modified oligonucleotide(dT)$_{25}$ (Thermo Fisher Scientific) or an unmodified oligonucleotide(dT)$_{25}$ as negative control (Thermo Fisher Scientific). Both oligonucleotides were provided as a 1 mM stock solution in DMSO. The mixture comprising the beads, oligonucleotide and salt was vortexed, sonicated for 1 min and incubated for 30 min at room temperature on a roller mixer. Immediately prior to use, 15 mg of EDC (Thermo Fisher Scientific) was dissolved in 100 μl of MES buffer (100 mM, pH 6.0) and 10 μL were added to the bead samples. The samples were mixed and incubated on a roller at room temperature overnight. The solution was removed from the beads and the beads were washed with 200 μL of water. The beads were then resuspended in 100 μL of 10 mM NaOH and heated to 70° C. for 20 minutes to eliminate residual RNAse activity and reduce unspecific coupling of oligonucleotides. The NaOH solution was removed and the beads were washed two times with 200 μL of water. The beads were resuspended in 100 μL of 50 mM Tris buffer pH 7.4, 0.1% Tween-20 and heated at 70° C. for 10 minutes. The beads were then washed with 200 μL of 50 mM Tris buffer pH 7.4, 0.1% Tween-20 two more times. Finally, the beads were stored in 100 μL of 50 mM Tris buffer pH 7.4 at 4° C. resulting in a bead concentration of 10 mg/mL. A parallel coupling procedure was performed under similar conditions with an aqueous buffer (e.g. 25 mM MES buffer pH 5.0 or 100 mM MES buffer pH 4.8) was used instead of DMSO (referred to as "standard procedure" herein).

Figure 4:
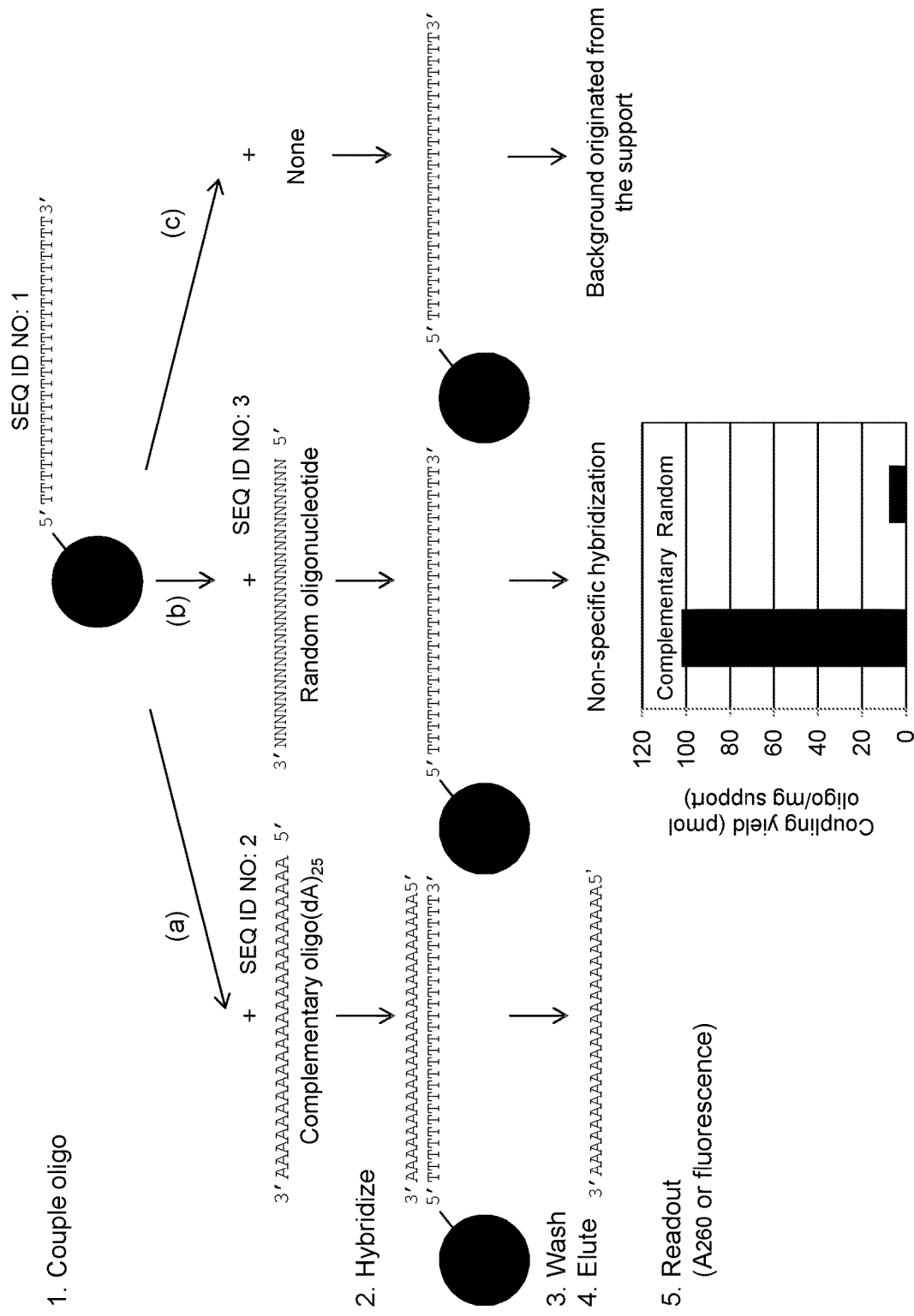
FIG. 4 is a schematic of a hybridization assay that can be used to determine nucleic acid coupling yield obtained with a standard procedure (in aqueous phase) or an improved coupling method (in organic phase) according to various embodiments.

FIG. 2A shows the coupling yields for Dynabeads™ M-270 Carboxylic Acid and FIG. 3A shows the coupling yields for Dynabeads™ MyOne Carboxylic Acid that were determined using the hybridization assay as described in Example 2 and FIG. 4. A complementary oligonucleotide (black bars) or a non-complementary oligonucleotide with random base composition (white bars) was used for subsequent hybridization with immobilized oligonucleotides. The data indicate that the yield of immobilized nucleic acid when aminated oligonucleotides (indicated by "+", as compared to unmodified oligonucleotides used as negative control indicated by "−") were coupled in the presence of an organic solvent instead of purely aqueous phase increased about 3-fold for Dynabeads™ M-270 Carboxylic Acid and about 1.8-fold for Dynabeads™ MyOne Carboxylic Acid, respectively (compare black bars of samples with aminated oligonucleotides). The percentage coupling efficiency was calculated by normalizing the coupling yield (reflected by the amount of hybridized complementary oligonucleotide) with the amount of oligonucleotide used for coupling. Coupling efficiencies achieved with the two different procedures are shown in FIGS. 2B and 3B, respectively.

Furthermore, the ratio of specific versus unspecific binding increased for both Dynabeads™ M-270 Carboxylic Acid ("M-270") and Dynabeads™ MyOne Carboxylic Acid ("MyOne") when the coupling was conducted in organic solvent as summarized in Table 1.

TABLE 1

Coupling Yield and Efficiency

| Sample | Coupling yield (pmol oligo/ mg beads) complementary | Coupling yield (pmol oligo/ mg beads) random | Coupling efficiency (%) complementary | Coupling efficiency (%) random |
| --- | --- | --- | --- | --- |
| M-270 coupled to unmodified oligonucleotide in aqueous solvent | 54.16 | 32.75 | 7.74 | 4.68 |
| M-270 coupled to aminated oligonucleotide in aqueous solvent | 64.11 | 27.30 | 9.16 | 3.90 |
| M-270 coupled to unmodified oligonucleotide in organic solvent | 37.24 | 15.60 | 5.32 | 2.23 |
| M-270 coupled to aminated oligonucleotide in organic solvent | 192.54 | 20.55 | 27.51 | 2.94 |
| MyOne coupled to unmodified oligonucleotide in aqueous solvent | 131.84 | 71.36 | 2.64 | 1.43 |
| MyOne coupled to aminated oligonucleotide in aqueous solvent | 184.03 | 41.54 | 3.68 | 0.83 |
| MyOne coupled to unmodified oligonucleotide in organic solvent | 15.05 | 20.37 | 2.15 | 2.91 |
| MyOne coupled to aminated oligonucleotide in organic solvent | 337.73 | 94.86 | 48.25 | 13.55 |

Example 2: Hybridization Assay

The coupling efficiency of aminated oligonucleotides to carboxylic acid solid support was indirectly determined using a hybridization assay as illustrated in FIG. 4. For this purpose 10 mg/mL of Dynabeads™ M-270 Carboxylic Acid loaded with oligo(dT)$_{25}$ (SEQ ID NO: 1) were mixed on a roller/rotator for 20 minutes at room temperature and 20 μL of the oligo(dT)-loaded bead were distributed into three 1.5 mL microtubes with screw caps. After adding 200 μL of hybridization buffer (0.9 M NaCl, 60 mM sodium phosphate buffer pH 7.4, 6 mM EDTA), the samples were vortexed, placed on the roller for 5 minutes, and placed on a magnet (DynaMag™-2; Thermo Fisher Scientific) for 30 seconds. After aspirating the supernatant was discarded, 200 μL fresh hybridization buffer was added to each tube and the beads were resuspended by pulse vortexing. A first sample of the beads was then supplied with 10 μL of a complementary oligo(dA)$_{25}$ (SEQ ID NO: 2) (FIG. 4, panel (a)), a second sample was supplied with 10 μL of a random oligonucleotide (SEQ ID NO: 3) (FIG. 4, panel (b)), and a third sample was supplied with 10 μL of buffer only (FIG. 4, panel (c)). The samples were then put on a roller for 10 minutes at room temperature to allow hybridization to occur. After removal of the supernatants, 200 µL of washing buffer (hybridization buffer with 0.1% Tween-20) as added and the samples were pulse vortexed until the beads were fully resuspended, followed by incubation on the roller for 5 minutes. The washing step was repeated twice before the tubes were placed on the magnet for 30 seconds and the supernatant was carefully removed. To elute the hybridized oligos, 20 µL of TE buffer (10 mM Tris buffer pH 8.0, 1 mM EDTA) was added to all tubes, and samples were pulse vortexed to fully resuspend the beads. The samples were then incubated at 80° C. for 5 minutes on a heating block before they were quickly spun down and placed on the magnet for 5-10 seconds until all beads were collected at the magnet. Eluates were then quickly transferred into fresh 1.5 mL microtubes to avoid re-hybridization. To determine the concentration of eluted oligonucleotide, the absorbance of each sample was measured three times at 260 nm with 2 µL of the eluates on a Nanodrop™ ND-1000 (Thermo Fisher Scientific). Measurement of the absorbance of samples (c) (negative control) was used for background correction. The amount of eluated complementary oligo reflects the yield of oligonucleotide covalently coupled to the beads, whereas the amount of eluated random oligo indicates non-specific hybridization to the covalently coupled oligonucleotides. The coupling efficiency was then calculated by normalizing the coupling yield with the amount of oligonucleotide used for coupling.

For an alternative readout, 10 µL of each eluate was transferred to a fresh tube, respectively. 590 µL of TE buffer were added to a total volume of 600 µL and samples were mixed thoroughly. For standard curves, a series of dilutions in TE buffer was prepared from complementary and random oligonucleotides, respectively, ranging from 0.0 to 1,562.5 ng/mL (0, 0.1, 0.5, 2.5, 12.5, 62.5, 312.5 and 1,562.5 ng/mL). 100 µL of the eluate dilutions and the standard samples were each dispensed into three wells of a 96-well plate, respectively. A 1:200 dilution of Quant-iT™ OliGreen™ ssDNA reagent (Thermo Fisher Scientific) in TE buffer was prepared and 100 µL thereof were dispensed into each well. Fluorescence in each well was then measured using a microplate reader (BioTek Instruments Inc).

Example 3: Effect of Salt and Amount of Organic Solvent on Coupling Yield and Unspecific Binding The effect of salt and the amount of organic solvent on the coupling yield and unspecific binding of nucleic acids to a carboxylate functionalized solid support was determined using a hybridization assay as described in Example 2.

In a first experiment Dynabeads™ MyOne Carboxylic Acid beads (Thermo Fisher Scientific) were coupled to oligo(dT)$_{25}$ in the presence or absence of either 0.2 M LiCl (FIG. 5A, left and right panels, respectively) or in the presence or absence of 0.2 M NaCl (FIG. 5B, left and right panels, respectively). The coupling reaction was conducted in the presence of 50% DMSO (FIG. 5A) or 90% DMSO (FIG. 5B) using either an aminated oligonucleotide (indicated by "+" in FIGS. 5A and B, respectively), or an unmodified oligonucleotide (indicated by "−") not carrying a terminal NH$_2$ group.

The data show that in the absence of salt (i) more nucleic acid (aminated as well as non-modified oligonucleotide) was coupled to the support (compare third and fourth columns of FIGS. 5A and B to first and second columns, respectively) and that (ii) the coupling yield increases for both types of oligonucleotide with higher amounts of organic solvent (compare third and fourth columns of FIGS. 5A and B, respectively). Furthermore the data indicate that (iii) the addition of salt has a stronger impact on unspecific than on specific coupling (compare differences in yield between "−" and "+" panels in the presence or absence of salt, respectively).

In a second experiment Dynabeads™ MyOne Carboxylic Acid beads (Thermo Fisher Scientific) were coupled to three different oligonucleotide sequences in the absence (FIG. 6A) or presence (FIG. 6B) of 0.2 M NaCl. The coupling reaction was conducted in the presence of 50% DMSO (FIGS. 6A and B, left panels) or 90% DMSO (FIGS. 6A and B, right panels), using either an aminated oligonucleotide (indicated by "+" in FIGS. 6A and B) or an unmodified oligonucleotide (indicated by "−") not carrying a terminal NH$_2$ group. Three exemplary oligonucleotides with different base composition (oligo(dN) with equivalent amounts of A, T, G and C, oligo(dA) enriched in A and T, and oligo(dGC) enriched in G and C) were assessed:

```
oligo(dN):
                                (SEQ ID NO: 4)
5'-TCATGATCCGGTGTACGGCACTAAC-3';

oligo(dAT):
                                (SEQ ID NO: 5)
5'-TCATAATCTAATGTAATGTACTAAC-3';

oligo(dGC):
                                (SEQ ID NO: 6)
5'-CCATGCCCTGGTGGACGGACCCGAC-3'.
```

Figure 6:
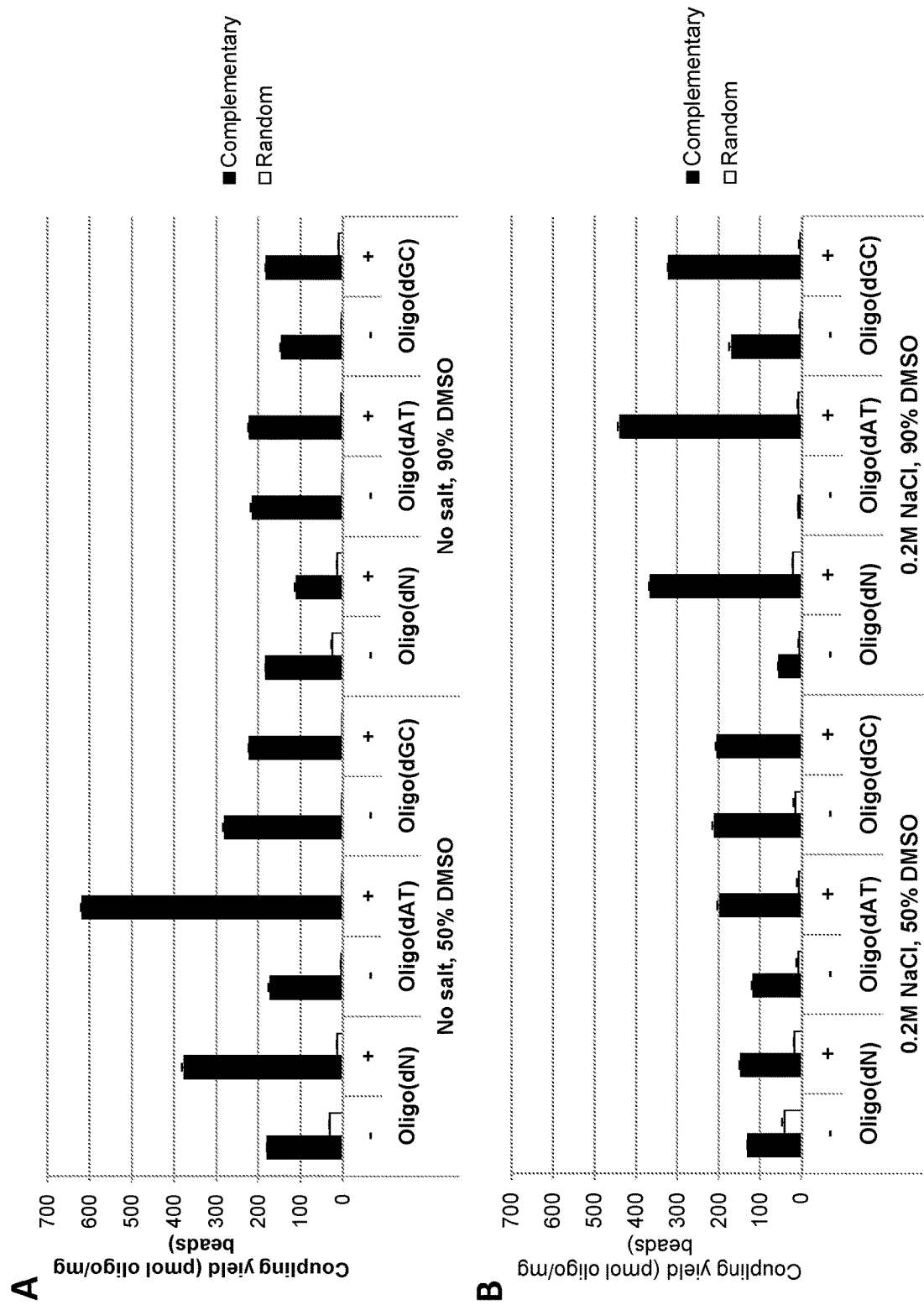
FIG. 6 shows the effect of the absence (A) or presence (B) of salt and different concentrations of DMSO on the coupling yield and non-specific binding of nucleic acid.

The data show that in the presence of salt and 50% DMSO both, unspecific and specific coupling were reduced (compare differences in yield between the left panels of FIGS. 6A and B, respectively). When the amount of organic solvent was further increased to 90% in the presence of salt, an increase of the specific coupling was observed for all tested oligonucleotides, whereas unspecific coupling was further reduced (compare differences in yield between "−" and "+" samples of left and right panels of FIG. 6 B).

In sum these data show that the addition of salt during the coupling reaction is capable of further reducing unspecific binding and that the overall binding yield can be modulated by the amount of organic solvent present during the coupling.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The invention claimed is:

1. A composition comprising:
   a solid support wherein carboxylic acid groups are covalently linked to the solid support,
   a nucleic acid comprising at least one primary amine function,
   a carbodiimide or derivative thereof, and
   an organic solvent.

2. The composition of claim 1, wherein at least a first portion of the carboxylic acid groups is modified with a reactive anhydride and at least a second portion of the carboxylic acid groups is bonded to the at least one primary amine function of the nucleic acid via a carbonylamide bond,
   and optionally an isourea by-product.

3. The composition of claim 1, wherein the solid support is selected from the group consisting of: particles, spheres, microparticles, nanoparticles, and beads.

4. The composition of claim 3 wherein the solid support is monodisperse.

5. The composition of claim 1, wherein the solid support is magnetic.

6. The composition of claim 1, wherein the solid support is beads having a nucleic acid coupling density of between about 40 and about 1,000 pmol/mg support, or between about 50 and about 800 pmol/mg support.

7. The composition of claim 1, wherein the organic solvent is selected from the group consisting of dimethyl sulfoxide, dimethylformamide, and diethyl sulfoxide or a mixture thereof.

8. The composition of claim 1, wherein the organic solvent is present at a concentration of at least about 50% and less than 95% per total volume.

9. The composition of claim 1 further comprising water or an aqueous buffer, wherein the concentration of water or aqueous buffer is less than 20% per total volume.

10. The composition of claim 1 further comprising water or an aqueous buffer, wherein the concentration of water or aqueous buffer is less than 10% per total volume.

11. The composition of claim 1, wherein the carbodiimide is EDC.

12. The composition of claim 7 wherein the aqueous buffer is MES or imidazole.

13. The composition of claim 1 having a pH of between about 4.5 and about 7.0.

14. The composition of claim 1 further comprising a salt.

15. The composition of claim 12, wherein the salt is LiCl or NaCl.

16. The composition of claim 14, wherein the salt is present at a concentration of at least about 0.1 M and less than about 1.0 M.

17. The composition of claim 1, wherein the nucleic acid is present at a concentration of between about 10 and about 10,000 pmol/mg support.

\* \* \* \* \*

SEQUENCE LISTING

```
Sequence total quantity: 6
SEQ ID NO: 1              moltype = DNA  length = 25
FEATURE                   Location/Qualifiers
source                    1..25
                          mol_type = other DNA
                          organism = synthetic construct
SEQUENCE: 1
tttttttttt tttttttttt ttttt                                                 25

SEQ ID NO: 2              moltype = DNA  length = 25
FEATURE                   Location/Qualifiers
source                    1..25
                          mol_type = other DNA
                          organism = synthetic construct
SEQUENCE: 2
aaaaaaaaaa aaaaaaaaaa aaaaa                                                 25

SEQ ID NO: 3              moltype =    length =
SEQUENCE: 3
000

SEQ ID NO: 4              moltype = DNA  length = 25
FEATURE                   Location/Qualifiers
source                    1..25
                          mol_type = other DNA
                          organism = synthetic construct
SEQUENCE: 4
tcatgatccg gtgtacggca ctaac                                                 25

SEQ ID NO: 5              moltype = DNA  length = 25
FEATURE                   Location/Qualifiers
source                    1..25
                          mol_type = other DNA
                          organism = synthetic construct
SEQUENCE: 5
tcataatcta atgtaatgta ctaac                                                 25

SEQ ID NO: 6              moltype = DNA  length = 25
FEATURE                   Location/Qualifiers
source                    1..25
                          mol_type = other DNA
                          organism = synthetic construct
SEQUENCE: 6
ccatgccctg gtggacggac ccgac                                                 25
```